United States Patent
Reichow et al.

[11] Patent Number: 6,129,435
[45] Date of Patent: Oct. 10, 2000

[54] DECENTERED PROTECTIVE EYEWEAR

[75] Inventors: Alan W. Reichow, Beaverton; Karl Citek, Hillsboro, both of Oreg.

[73] Assignee: Nike, Inc., Beaverton, Oreg.

[21] Appl. No.: 09/058,118

[22] Filed: Apr. 9, 1998

[51] Int. Cl.⁷ ................................................ G02C 7/02
[52] U.S. Cl. ........................... 351/41; 351/159; 351/178
[58] Field of Search .............................. 351/41, 159, 178

[56] References Cited

U.S. PATENT DOCUMENTS

| | | | |
|---|---|---|---|
| 1,332,410 | 3/1920 | Potts | 351/41 |
| 1,354,040 | 9/1920 | Hammon | 351/41 |
| 1,536,828 | 5/1925 | Drescher | 351/41 |
| 1,619,314 | 3/1927 | Gagnon | 351/41 |
| 1,697,030 | 1/1929 | Tillyer | 351/41 |
| 1,741,536 | 12/1929 | Rayton | 351/41 |
| 1,910,466 | 5/1933 | Glancy | 351/41 |
| 1,942,400 | 1/1934 | Glancy | 351/41 |
| 2,406,608 | 8/1946 | Joyce | 351/41 |
| 2,442,849 | 6/1948 | Glazer | 351/41 |
| 3,229,303 | 1/1966 | Jonassen | 351/41 |
| 3,434,781 | 3/1969 | Davis et al. | 351/41 |
| 4,271,537 | 6/1981 | Bowlus et al. | 351/41 |
| 4,271,538 | 6/1981 | Montesi et al. | 351/41 |
| 4,515,448 | 5/1985 | Tackles | 351/41 |
| 4,613,217 | 9/1986 | Fuerter et al. | 351/41 |
| 4,617,686 | 10/1986 | Nahas | 351/41 |
| 4,741,611 | 5/1988 | Burns | 351/41 |
| 4,761,315 | 8/1988 | Logan et al. | 351/41 |
| 4,859,048 | 8/1989 | Jannard | 351/41 |
| 4,867,550 | 9/1989 | Jannard | 351/44 |

(List continued on next page.)

FOREIGN PATENT DOCUMENTS

| | | |
|---|---|---|
| 0456321 | 5/1949 | Canada. |
| 121 018 A2 | 10/1984 | European Pat. Off.. |
| 2626683 | 8/1989 | France. |
| 2740231 | 10/1995 | France. |
| 1765802 A1 | 9/1992 | U.S.S.R.. |
| 2278459 | 11/1995 | United Kingdom. |
| WO97/35224 | 9/1997 | WIPO. |

OTHER PUBLICATIONS

Amster, C.S., "Vertical Decentration of a Prescription Lens and its Effects on Visual Acuity," *The Opthalmic Optician*, 43–44 (Jan. 22, 1997).

Bechtold, E.W. et al., "The Effect of Pantoscopic Tilt on Opthalmic Lens Performance," *American Academy of Optometry*, 42(9): 515–524 (Sep. 1965).

(List continued on next page.)

*Primary Examiner*—Huy Mai
*Attorney, Agent, or Firm*—Klarquist Sparkman Campbell Leigh & Whinston, LLP

[57] ABSTRACT

Noncorrective protective eyewear with lateral wrap and pantoscopic tilt introduce prismatic distortion and astigmatism into lenses that interfere with good optical performance. The lenses of this invention have an optical axis that is deviated away from the line of sight, in a direction generally opposite the inward tilt of the lateral wrap and/or the incline of pantoscopic tilt, to offset the tilt induced prism. Low power may be introduced into the lenses to decrease their taper, further offset the tilt induced prism and astigmatism (particularly in peripheral fields of view), lessen weight, provide better physical stability, and allow more uniform light transmission than plano lenses. The lenses may be cut from lens blanks in which the A line of the lens is at a non-zero angle to an equator of the lens, and the optical center of the lens may be horizontally and vertically displaced from the geometric center of the lens, and even off the lens altogether. This invention provides greater versatility in cutting a lens from a lens blank in a position that avoids peripheral irregularities in the molded lens blank, while significantly decreasing tilt induced prism, yoked and vergence demands, and astigmatic blur along the line of sight and peripherally.

48 Claims, 9 Drawing Sheets

U.S. PATENT DOCUMENTS

| | | | |
|---|---|---|---|
| 4,969,649 | 11/1990 | Lugiewicz | 351/44 |
| 5,050,979 | 9/1991 | Shinohara | 351/41 |
| 5,131,101 | 7/1992 | Chin | 351/41 |
| 5,208,614 | 5/1993 | Jannard | 351/44 |
| 5,390,369 | 2/1995 | Tubin | 351/41 |
| 5,444,501 | 8/1995 | Aloi et al. | 351/41 |
| 5,457,502 | 10/1995 | Iida | 351/41 |
| 5,541,674 | 7/1996 | Jannard | 351/44 |
| 5,555,038 | 9/1996 | Conway . | |
| 5,614,964 | 3/1997 | Garneau | 351/83 |
| 5,638,145 | 6/1997 | Jannard et al. | 351/44 |
| 5,648,832 | 7/1997 | Houston et al. | 351/44 |
| 5,689,323 | 11/1997 | Houston et al. | 351/44 |

OTHER PUBLICATIONS

Brooks, C.W., *Essentials for Ophthalmic Lens Work*, Butterworth–Heinemann, Boston (1983).

Cohen, S., "Importance of Pantoscopic Angle," *Journal of the American Optometric Association*, 36(10):916–918 (Oct. 1965).

Davis, J.K., "The Optics of Plano Lenses," *American Journal of Optometry and Archives of American Academy of Optometry*, 540–556 (Oct. 1957).

Davis, J.K., "Geometric Optics in Opthalmic Lens Design," in Smith, W.J., *Proceedings of the Society of Photo–optical Instrument Engineers, Applications of Geometrical Optics*, San Diego, California, SPIE 39:65–100 (Aug. 27–29, 1973).

Davis, J.K., "A Polycarbonate Ophthalmic–Prescription Lens Series," *American Journal of Optometry and Physiological Optics*, 55(8): 543–552 (Aug. 1978).

Duke–Elder, S., "Centring and Decentring of Lenses," *The Practice of Refraction*, $8^{th}$ Edition, J & A Churchill Ltd., London: 273–275 (1969).

Duke–Elder, S. et al., *System of Ophthalmology, Ophthalmic Optics and Refraction*, vol. 5, The C.V. Mosby Company, St. Louis: 678–680 (1970).

Emsley, H.H. et al., *Ophthalmic Lenses*, Hatton Press Ltd., London: 78–85 (1951).

Fry, G.A. et al., "The Major Reference Point in a Single Vision Lens," *American Journal of Optometry and Archives of American Academy of Optometry*, 24(1): 1–7 (Jan. 1947).

Fry, G.A., "The Boxing Method of Specifying Eye Size," *Journal of the American Optometric Association*, 481–484 (Feb. 1959).

Fry, G.A., "Face–Form Frames," *Journal of the American Optometric Association*, 49(1): 31–38 (Jan. 1978).

Patent Specification: Gatten, "Ophthalmic Lens for Spectacles Affording Increased Field of Vision," No. 680,400 (Oct. 1, 1952).

Reichow, A., Declaration dated Sep. 30, 1997 submitted in Oakley, Inc. vis. Nike, Inc., Civil Action No. SACV–97–606 AHS (EEx) filed in the U.S. District Court for the Central District of California.

Woods, T.A., "Ophthalmic Lenses for Athletes and Sportsmen," *Optometry Clinics*, 3(1):33–55, (1993).

*ACTA Ophthalmologica*, vol. 60, Supplementum 151: 5–30 (1982).

Internet: "Will Shooting Glasses Improve Your Shotgun Game?" Custom Sportswear & Optical, http://www.customsportswr–optical.com/article.html.

Internet: "Shooting Glasses: Jaggi Shooting Frames and Accessories," Champion Shooters Supply, http://www-.championshooters.com/glasses.html.

Internet: "Sport Glasses by Decot Hy–Wyd," Decot Hy–Wyd, Inc., http://www.sportglasses.com/intro.html, http://www.loader6.com/decot2.html.

Internet: "Sporting Glasses," Napier Optical, http://www.napieruk.com/glasses.html.

Internet: "Hunting," Sport Eyes, http://www.sporteyes.com/hunting.html.

Internet: "The Finest Tailor–made Shooting Sportswear," Custom Sportswear & Optical, http://www.customsportswr–optical.com/about.html, http://www.customsportswr–optical.com/eyewear.html.

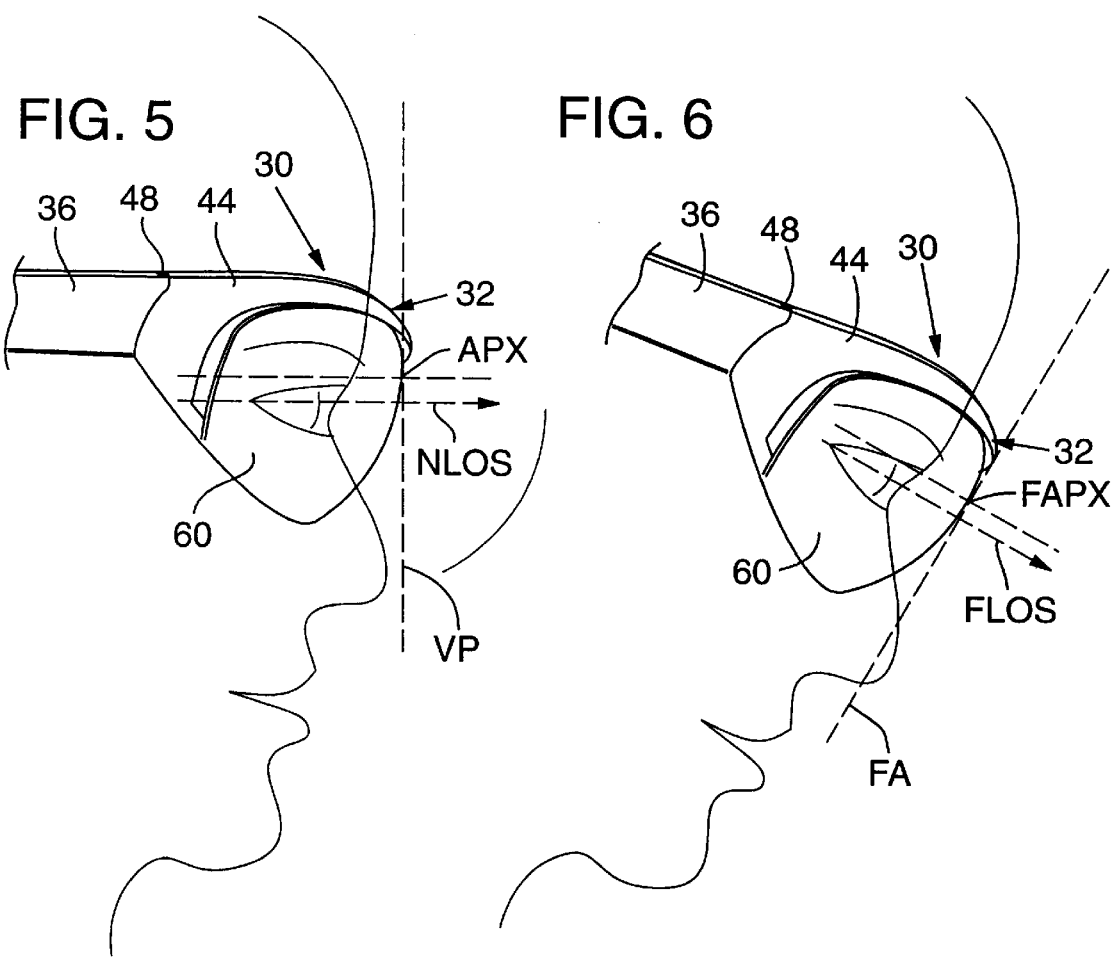

DECENTERED PROTECTIVE EYEWEAR

FIELD OF THE INVENTION

This invention concerns protective eyewear, particularly protective or non-corrective eyewear with decentered optics.

BACKGROUND OF THE INVENTION

A serious obstacle to the more ubiquitous use of protective eyewear (such as sunglasses and goggles) is that protective lenses can distort vision. This distortion has been thought to be caused by unwanted dioptric power or prismatic effects in the lens, which has been particularly severe in protective lenses that are designed to curve around the eye to the side of the head ("wrap") and/or tilt inward toward the cheekbone (pantoscopic tilt). Although wrap and tilt are aesthetically pleasing, and can provide superior physical protection of the eye, they can also cause the normal line of sight of the eye to strike the lens surface at an angle. This relationship has caused optical distortion that is distracting to the wearer, and presents a serious problem to persons who require precise visual input, such as athletes, pilots and surgeons. This distortion can also be problematic when performing even more common tasks.

The prior art is replete with examples of efforts to overcome optical distortion in protective eyewear. At first such lenses were made with concentric surfaces having no optical center or optical centerline, but the lenses had inherent minus power (which was considered undesirable), and excessive prismatic distortion along the line of sight and peripherally. Later lenses were made plano (zero power), and centered with the optic center at the geometric center of the lens aperture or eyewire, but the plano lenses were found to induce base out prism along the line of sight, and had poor peripheral optics.

Rayton's U.S. Pat. No. 1,741,536 (issued in 1929 to Bausch & Lomb) disclosed a protective goggle in which the front and back surfaces of the lenses were defined by two spheres of different radii having offset centers. An optical axis through the centers of the spheres was spaced from, and oriented parallel to, a line of sight. This optical configuration provided a tapered lens, in which the lens thickness gradually decreased from the optical center toward the edges. Maintaining the line of sight parallel to the optical axis helped neutralize the distortion that would otherwise be caused by wrapping the lenses laterally with respect to the eye.

In the 1980s, the Foster Grant Company sold dual lens Eyeguard protective eyewear, which held a tapering spherical lens in front of each eye with both wrap and pantoscopic tilt. The optical axis of each lens was horizontally and vertically spaced from, and maintained parallel to, the normal line of sight. This same concept was again claimed many years later in U.S. Pat. Nos. 5,648,832 and 5,689,323, which issued to Oakley, Inc. The parallel relationship between the optical axis and normal line of sight was found to be partially successful in minimizing optical distortion caused by wrap and pantoscopic tilt, but these lenses still had undesired peripheral performance, with prismatic effects that produced yoked and vergence demands.

U.S. Pat. Nos. 4,271,538 and 4,964,714 disclosed a similar position of the optical centerline in safety spectacles, where the optical centerline was horizontally and vertically displaced from, and parallel to, a normal line of sight. However, the '538 patent itself acknowledged that this relationship left a prismatic imbalance between the right and left eyes, that imposed a vergence demand on the eyes. Like the Foster Grant and Oakley eyewear, these lenses also suffered from undesired peripheral performance, with prismatic imbalance between the eyes that produced yoked and vergence demands.

In the correction of ordinary refractive errors such as myopia and hyperopia, the optical axis of a corrective lens may be slightly tilted from the normal line of sight. A slight downward decentration is commonly used in lenses that have pantoscopic tilt, to help keep the optical axis of the lens directed through the center of rotation of the eye. In a lens having 5–10 degrees of pantoscopic tilt, for example, the optical axis is often shifted about 3 mm below the normal line of sight. A deliberate decentration of a corrective lens may also be needed to compensate for misalignment of the eyes (such as phorias and tropias).

Decentered lenses may be manufactured by cutting a lens blank away from the geometric center of the lens blank. However, the periphery of an injection molded lens blank often includes optical irregularities, and those irregularities are incorporated into a lens which is cut from the edge of the blank. If the decentration is large, the dimensions of the lens must be small so that it can be cut from the lens blank. Alternatively, a larger lens blank can be used, but this solution leads to an inefficient use of large (and relatively more expensive) lens blanks. This problem is particularly acute for lenses manufactured in large quantities, where an incremental increase in the size of the lens blank can significantly increase the manufacturing cost.

It is an object of one embodiment of this invention to minimize optical distortion in protective and noncorrective lenses.

An object of an alternative embodiment of the invention is to provide a more efficient manufacturing method for decentered lenses.

SUMMARY OF THE INVENTION

The foregoing problems are addressed by the low minus power lenses of the present invention, which have an optical axis that is angularly deviated at a sufficient angle away from parallel with the line of sight to minimize prismatic distortion, both along a line of sight and peripherally in the field of view. This lens is particularly adapted for protective, non-corrective eyewear in which the lens is mounted in a tilted orientation with respect to the line of sight. The optical axis of the lens is angularly deviated in a direction generally opposite the direction that the low minus power lens is to be tilted, which has surprisingly been found to minimize optical distortion in the lens. This design contravenes the longstanding teaching in the art (since the 1929 Rayton patent), that the optical centerline in non-corrective lenses must be maintained as parallel as possible to the line of sight. The present design has surprisingly been found to reduce both yoked and vergence demands, as well as astigmatic blur, in eyewear made with such lenses.

This invention has taken advantage of the inventors' recognition that tilting a non-corrective plano lens toward the face induces prism base in the direction in which the lens is tilted. For example, when the inferior edge of a lens that is mounted with pantoscopic tilt is inclined toward the face, base down prism is induced. In accordance with the present invention, the optical axis of a low power lens is deviated generally superiorly, in a direction substantially opposite the direction of the prism induced by the tilt, to offset the tilt induced prism. Similarly, a lens mounted with lateral wrap (temporal edge inclined towards the face) has been found to induce base out prism, which is offset in accordance with the present invention by angular deviation of the optical axis of a low power lens in a generally nasal direction. Lenses that are to be mounted with pantoscopic tilt and lateral wrap may therefore have an optical axis that is deviated both superiorly and nasally to minimize the prism induced by the tilt. Optical compensations for other directions of lens tilt can similarly be achieved by deviating the optical axis generally away from the inward tilt of the lens.

The low power lens may have any amount of minus power, up to that for a concentric lens for a given base curvature. Low power lenses may, for example, have more minus power than −0.005, for example more than −0.01 or −0.02 and particularly in the range of −0.01 to −0.12 diopters, for example −0.04 to −0.09 diopters. The use of such low minus power is contrary to the teaching of the art, which has been that plano (non-power) lenses were essential for protective eyewear that does not distort the vision of the wearer. By going against the teaching of the art, the inventors have achieved a number of advantages. The low power lenses have less taper, and can be thinner than zero power lenses. The reduction in taper produces a corresponding reduction in peripheral prism that would otherwise be induced by the excessively non-parallel surfaces of the plano lenses. Thinner lenses also provide better physical stability, improved optical quality, lower weight, and more uniform light transmission than plano lenses. A physiologic advantage of the low minus lens is that it better matches the accommodative posture of athletes and other persons engaged in highly visually demanding and/or stressful activities.

The versatility of the present invention allows it to be applied to a wide variety of lenses having different degrees of lateral wrap, pantoscopic tilt, powers, center thicknesses, and lens surface curvatures, because the prism induced by the tilt ("prism by tilt") can be neutralized by altering a number of these factors. Hence a lens with substantial pantoscopic tilt may have a larger separation between the apex and the line of sight, and a corresponding increase in prism by tilt. This prism can be reduced by one or more of a combination of parameters, such as increasing the angle of deviation between the line of sight and optical axis, increasing the minus power of the lens, or reducing the base curvature of the lens.

The present invention is particularly well adapted to high base lenses, which are at least base 4 lenses, for example a base 6–9 lens, and a base 6 lens in particular embodiments. The lens is also particularly suitable for use in dual lens eyewear, with lenses having a center thickness of about 1–3 mm (for example about 1.5–2.25 mm), a power of about −0.01 to −0.12 (particularly about −0.04 to −0.09), a pantoscopic tilt of 3–20 degrees, and lateral wrap of 5–30 degrees. In particular embodiments, the lens is a 6 base lens with a center thickness of about 1.6 mm, a power of about −0.045 diopters, and the tilted orientation of the lens includes lateral wrap of about 15 degrees, a pantoscopic tilt of about 12.5 degrees, and the angular deviation between the optical axis and the line of sight (or a parallel to the line of sight) is about 22–23 degrees nasally and 18–19 degrees superiorly.

The lenses of the present invention may be spherical, cylindrical, toroidal, elliptical, or of other configurations known in the art. However, the particularly disclosed embodiment is a spherical lens in which a substantially spherical anterior surface substantially conforms to a first sphere having a first center, and a substantially spherical posterior surface substantially conforms to a second sphere having a second center. The radius of the first sphere is greater than a radius of the second sphere, so that a lens thickness tapers away from an optical center of the low power lens (which may be on or off the lens), and an optical axis extends through the first and second centers of the spheres and the optical center of the lens. This optical axis is angularly rotated nasally and superiorly away from the parallel with the line of sight (to compensate for lateral wrap and pantoscopic tilt), to a sufficient extent to substantially offset prism induced by tilt (for example reducing prism by at least 25%, 50%, 75%, or 100%). This angular deviation provides a lens having a broad spectrum of improved optical properties, including reduced prism (to substantially zero along a functional line of sight in optimal embodiments), reduced astigmatic blur along both the line of sight and peripherally, and reduced yoked and vergence demands.

Another independent aspect of the invention is that the lens may be cut from a lens blank with the A line of the lens angled at a non-zero acute angle to the equator of the lens, from which the lens vertically tapers symmetrically. In particular embodiments, an optical center of the lens blank is displaced along the equator of the lens, away from the geometric center of the blank, although in other embodiments the optical center may also be displaced in the direction of the vertical meridian of the lens (which vertically bisects the equator), so that the optical center is not positioned along the equator, and in particular is not on either the equator or vertical meridian. In some particularly advantageous embodiments, the optical center is not on the lens blank at all. The optical center may be displaced along a line coincident with the equator, and under certain conditions is more advantageously vertically displaced from the equator so that the optical center is on a line that extends through the geometric center of the blank at an acute, non-zero angle.

The invention includes methods of manufacturing lenses, using these and other blanks, in which an optically corrected, protective lens is to be mounted in a tilted orientation in a frame. The lens is cut from a lens blank at a position such that an optical axis of the lens is to be horizontally and vertically displaced from a line of sight, and angularly deviated to the line of sight at an angle sufficient to offset at least some (and preferably substantially all) of the prismatic distortion along the line of sight, and most of the prismatic distortion in the periphery, which has been introduced into the lens by the tilted orientation. Hence, the lens outline is deliberately displaced from the equator and angled in both a horizontal and vertical direction with respect to the equator and vertical meridian of the blank, such that the A line of the lens is oriented at a non-zero angle with respect to the equator. When the lens is rotated around or with respect to the optical center, so that the position of the optical center in relationship to the lens shape is not changed, the optical and geometric characteristics of the lens are preserved. This method allows the lens blank to be used more efficiently, and permits flexibility in positioning the lens in a position that avoids injection mold gate irregularities and peripheral plastic distortions inherent in many lens blanks.

The foregoing and other objects, features, and advantages of the invention will become more apparent from the following detailed description of several embodiments of the invention, which proceeds with reference to the accompanying drawings.

BRIEF DESCRIPTION OF THE DRAWINGS

FIG. 5 is side view of the eyewear in place on a human head, with the head in an upright orientation with the normal line of sight directed straight ahead.

FIG. 6 is a view similar to FIG. 5, showing the head tilted down and the eye position lowered to perform a specific task, such as trail running.

DETAILED DESCRIPTION

The present invention concerns optically decentered protective eyewear, for example noncorrective protective eyewear having both wrap and pantoscopic tilt, but which still provides optically balanced visual performance, for example over a wearer's field of view. The balanced optical performance is achieved in a decentered lens in which the optical axis of the lens is tilted away from a line of sight, such as a functional line of sight (FLOS), including the straight ahead normal line of sight (NLOS).

Lines of Sight, Geometric Center and Apex

Figure 1:
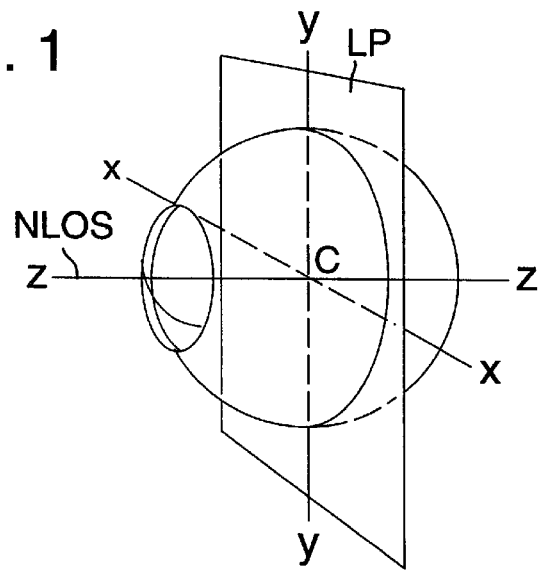
FIG. 1 is a schematic view of several anatomic reference planes through the eye.
Figure 2:
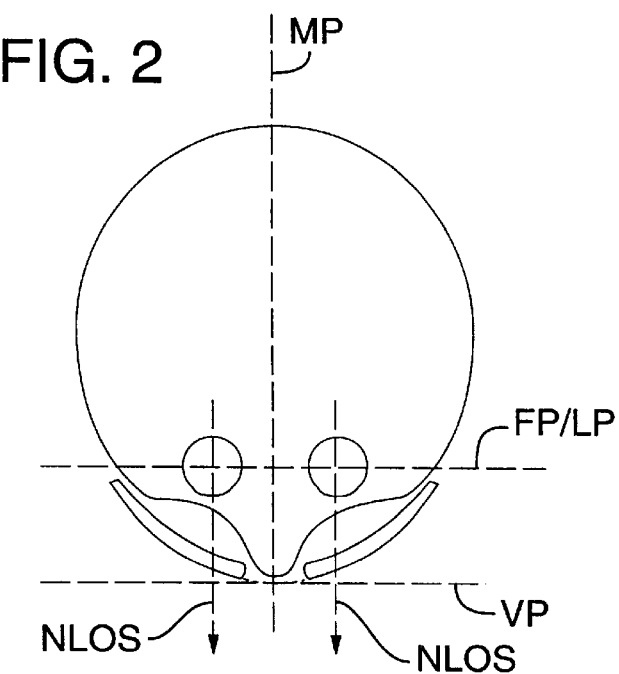
FIG. 2 is a schematic top view of the human head with high wrap lenses placed in front of the eye.
Figure 3:
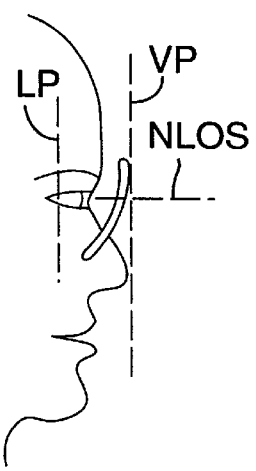
FIG. 3 is a side view of the schematic head shown in FIG. 2.

The explanation of this invention will be facilitated by an understanding of several imaginary anatomic reference planes in the human head and body, which are illustrated in FIGS. 1–3. A median plane (MP in FIG. 2) is a unique plane that passes longitudinally through the middle of the body from front to back and divides the head into right and left halves. A frontal plane (FP in FIG. 2) is any one of a series of planes passing longitudinally through the body from side-to-side, at right angles to the median plane, and dividing the body into front and back parts. Any frontal plane and the median plane are perpendicular to one another.

Listing's plane (LP in FIGS. 1–3) is a particular frontal plane that is further defined as a transverse vertical plane perpendicular to the anteroposterior axis of the eye, and containing the center of rotation of the eyes. Listing's plane (LP) is perpendicular to the visual fixation axis z (FIG. 1), which extends straight ahead of the eye in the primary position with the head looking straight ahead. Listing's plane lies in the plane defined by the transverse horizontal axis of rotation x and the vertical axis of rotation y. The theoretical normal line of sight (NLOS) is along the z axis, through the center of rotation CR of the eye in the primary position with the body and head erect, perpendicular to Listing's plane (LP) and other frontal planes (FP), and parallel to the median plane MP.

The normal line of sight is a fixed line that projects forward from the eye along the z axis shown in FIG. 1, and that line of sight is not normally understood to vary in a given individual. However the normal line of sight may vary (both horizontally and vertically) between individuals, because of variations of head and face morphologies (such as the distance between the eyes, and the location of the nasion and ears) which determine an as worn orientation of eyewear. Moreover, the normal line of sight may vary vertically between the right and left eye of a given individual, because of facial asymmetry. The "normal" line of sight is therefore often determined on a head form, such as the Alderson head form, or the more current and accurate Canadian head form, in which a statistically average position of a line of sight has been determined. But the NLOS may also be determined as a special case of the functional line of sight (FLOS), using the techniques described later in this specification for finding a FLOS.

Figure 4:
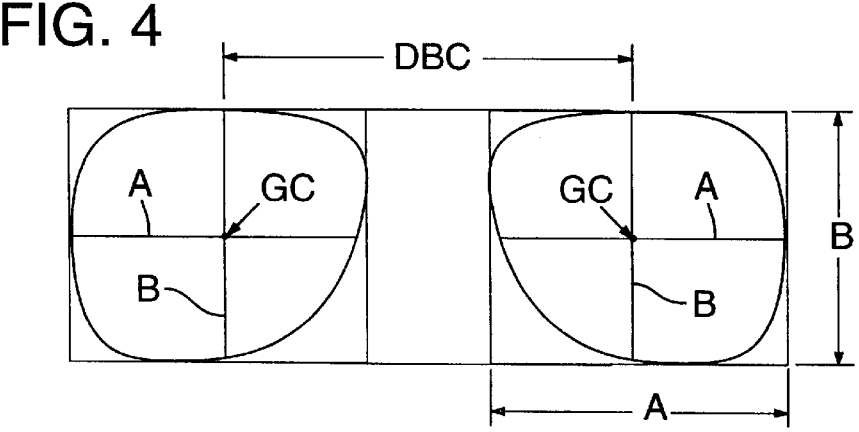
FIG. 4 is a schematic view of the reference system used to describe lenses mounted in optical frames.

The geometric center of a lens (GC in FIG. 4) is defined as the geometric center of a rectangle that circumscribes each frame lens aperture from a frontal perspective. The location of the geometric center can easily be located at the intersection of diagonals of each rectangle, or the intersection of perpendicular bisectors of the horizontal and vertical dimensions, which are respectively referred to as the A line and the B line.

The apex of a lens is a measurement that reflects the head position of the person wearing the lens, the orientation of the lens as it is held by the frame, and the fit of the frame on the head of the wearer. In prior optical work, the apex was understood to be the forwardmost point of the lens, that was tangent to a vertical plane (VP) (a frontal plane), as shown in FIGS. 2 and 3, that was perpendicular to the theoretical NLOS. The apex is the point on each lens that would simultaneously first contact the vertical frontal plane VP as the eyewear approaches that vertical plane, if the eyewear is held in the orientation it has on the head of the person looking straight ahead, as shown in FIG. 3. If the lens is extremely tilted forward (high pantoscopic tilt), the apex may be superior to the lens on an imaginary continuation of the lens surface, or in extremely laterally tilted lenses (high wrap) the apex may be nasal to the lens on an imaginary continuation of the lens surface.

Definition of Functional Line of Sight

The line of sight and apex will often change, depending on the task a person is performing, as illustrated in FIGS. 5 and 6. FIG. 5 shows the location of a typical apex (APX), where the vertical plane touches the forwardmost position of each of the right and left lenses, perpendicular to the NLOS. FIG. 6, however, illustrates a functional apex plane (FA), having a functional apex (FAPX) at the intersection of the plane FA and the forwardmost point of the lens relative to the plane FA. The plane FA is perpendicular to the functional line of sight (FLOS). The functional line of sight is the line along the fixation axis of the eye when the eye and head are directed in a preferred position for performing a particular visual function or task (e.g. trail running, volleyball, surgery, or driving). In trail running, for example, the eye may be rotated around the x axis (FIG. 1) such that the visual fixation axis through the center of the pupil is lowered in the y-z plane about 15 degrees below the z axis.

In addition to the downward rotation of the eyes, the head may also tilt forward (for example by about another 15 degrees) as shown in FIG. 6. The total downward visual deviation is the sum of the rotation of the eyes and the downward tilt of the head (if the head tilt and eye rotation are in the same direction), or about 30 degrees total in this example. The functional apex FAPX is the point on each lens (or an imaginary extension of the lens) that is tangent to the plane FA which is perpendicular to the functional line of sight FLOS, and that touches the forwardmost portion of the lens (or an imaginary extension of the lens) as the plane is brought toward the lens while held perpendicular to the functional line of sight FLOS.

There are several approaches to determining the functional line of sight, and the corresponding functional apex. A population of persons performing a task can be observed performing the task, and each of their lines of sight marked on the lenses of eyewear they are wearing (or photographs taken of the pupils through the lenses) to arrive at a norm for the functional line of sight. Alternatively, infrared pupil position detectors can be worn by persons performing the tasks, and the pupil positions determined remotely. In addition, video analysis of head and body position can be performed. The functional line of sight can be determined for an individual (if custom lenses are being made), or an average position of the functional line of sight can be determined for a population of persons who perform the activity. The lenses can then be worn by persons performing the function for which the lenses are designed, and refinements made to the position of the optical axis based on the visual performance and comfort of the wearer.

As used in this specification, the "line of sight" includes specific cases which are the normal line of sight and the functional line of sight. A functional line of sight can also be the normal line of sight, when the visual demands of a function are in the straight ahead position. A "nasal" direction is generally toward the nose, and a "temporal" direction is generally toward the temple. A "superior" direction is generally upward and an "inferior" direction is generally downward.

Prismatic Distortion

A lens produces a linear displacement, or foreshortening, of an image if the image is viewed along a direction of gaze that is not along the optical axis of the lens nor along the normal to the surface of the lens. A lens also produces an angular displacement, or prismatic deviation, if the image is viewed along a direction of gaze parallel to the optical axis but displaced from it; this defines a decentered lens. Prismatic deviation likewise may be induced if the direction of gaze is not parallel to the optical axis, regardless of where on the lens the direction of gaze intersects the surface. When the direction of gaze is not coincident with the optical axis of a lens, the lens will typically produce a total deviation, which is a combination of foreshortening and prismatic deviation.

Conventionally, the amount of the prismatic deviation is measured in prism diopters (pd) and is calculated using Prentice's rule:

$$\text{Prism}(pd) = \frac{\delta}{f} = \delta P$$

where P is the lens power measured in diopters (D), $f$ is the lens focal length in meters, and $\delta$ is the decentration in centimeters, where decentration refers to the direction and magnitude that the optical center is moved relative to the line of sight. The decentration can be horizontal, vertical, or oblique, but is generally evaluated in terms of horizontal and vertical deviations. A horizontal decentration of a non-plano lens with respect to an eye generally produces a horizontal prismatic deviation. A nasal decentration of a positive power lens produces a prismatic deviation that is referred to as "base-in" prism. Similarly, a temporal decentration of a positive power lens produces a prismatic deviation referred to as "base-out" prism. Nasal and temporal decentrations of a minus power lenses produce base-out and base-in prism, respectively.

To compensate for horizontal prism in eyewear, the eyes must rotate horizontally by angles approximately equal to the prismatic deviations. If the prismatic deviations for both eyes have the same magnitude and direction, the NLOS is deviated, but the eyes move in a so called "yoked" alignment. If the prismatic deviations differ in magnitude or direction, a relative motion of an eye or eyes toward (convergence) or away from each other (divergence) is required to avoid diplopia (double vision). The differences in prismatic deviation thus give rise to a disjunctive or vergence demand that is quantified as the net prismatic deviation obtained by combining the individual prismatic deviations. The vergence demand can require either a convergence or a divergence of the eyes, but is referred to as a vergence demand in either case. Particularly for visually demanding activities such as athletic activities, the yoked and vergence demands should be kept small in order to permit accurate spatial perception and anticipation timing, and to avoid eye fatigue. However even casual wearers of eyewear are more comfortable if the yoked and vergence demands are decreased.

Figure 7:
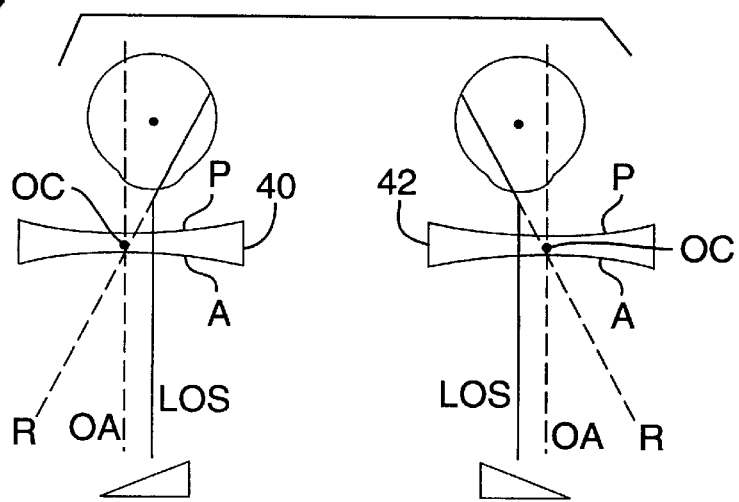
FIG. 7 is a schematic horizontal sectional view illustrating optical distortion induced by base in prism in both the right and left lenses.
Figure 8:
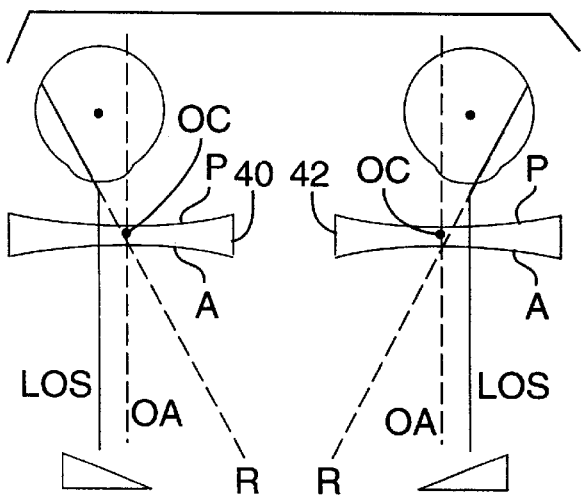
FIG. 8 is a view similar to FIG. 7, illustrating optical distortion induced by base out prism in both lenses.

The vergence resulting from prismatic deviations for both eyes depends on both the magnitude and direction of the prismatic deviations. For example, eyewear shown in FIG. 7 has a right lens 40 and a left lens 42. The lenses 40, 42 are negative power lenses having the same power or focal length. Each lens has an optical center OC on an optical axis OA coincident with a line through the centers of curvature of the anterior surface A and a posterior surface P of each lens. The optical center of each lens is shifted temporally from the line of sight LOS (temporal decentration), which induces a base in (BI) prism for each eye. The base in prism makes light rays R from a frontal distant object appear to diverge so that the object appears farther than it really is. FIG. 8 shows a similar situation in which the optical center OC of each lens is nasally decentered, which induces a base out prism for each eye, making an object appear closer than it actually is. Research demonstrates that athletes generally are more sensitive to and can tolerate less error in horizontal and vertical induced prism than non-athletes.

Figure 9:
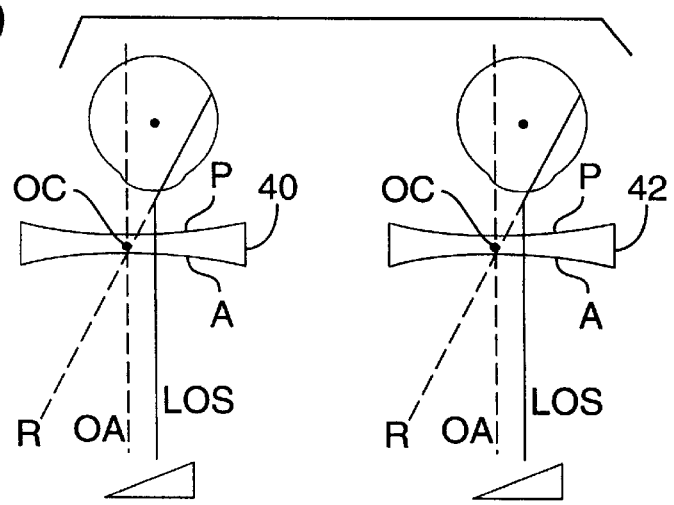
FIG. 9 is a schematic view illustrating the optical effect of base in prism in front of the right eye and base out prism in front of the left eye.

FIG. 9 illustrates a situation in which a right lens induces base in prism, while the left lens induces base out prism. Light rays R from an object that is straight ahead instead appears to be shifted to the right of the field of view, which causes the eyes to deviate rightward. If the amount of prism induced for each eye is the same, the eyes will move together in a "yoked" rotation to the right. If the amount of prism for each eye is not equal, then an additional vergence demand is imposed on the eyes, in which there must be relative movement of one or both of the eyes toward (convergence) or away (divergence) from each other. Such vergence is often incomplete, which can result in diplopia or poor perception. Even if the vergence is complete, it induces oculomotor strain that is uncomfortable for the wearer.

Vertical prism effects are generally divided into base-up (BU) and base-down (BD) prism. The same problems discussed with respect to BO and BI prism apply to vertical prism, but are usually even less well tolerated by the wearer.

The amount of horizontal prism can vary across the lens, and imbalance can become more of a problem peripherally, where one eye is looking through a nasal portion of a lens while the other eye is looking through a temporal portion of the lens. The amount of vertical prism can also vary across the lens in a similar fashion when the eye is looking through a superior or inferior portion of the lens. This variation can create inaccuracies in visual perception across the field of view that are difficult to compensate, and are troublesome in recreational or sporting activities that demand accurate visual input.

Prism in High Base Curve Protective or Non-Corrective Lenses

By convention, the curvature of the anterior surface of a lens is called the base curvature and is defined as 530/R, where R is the radius of curvature of that surface in millimeters. A line through the centers of curvature $C_1$ (of the anterior surface) and $C_2$ (of the posterior surface) defines an optical axis OA that intersects the lens (or an imaginary extension of the lens) at an optical center OC. The lens (or its imaginary extension) has a thickness CT along the optical axis OA, and tapers symmetrically away from or towards the optical center OC. The radius of curvature $R_2$ of the posterior surface is selected in combination with the center thickness CT and the base curvature radius $R_1$ to provide a predetermined lens power. The radius $R_2$ for a selected lens power P is readily calculated using the standard formula for lens power:

$$P = (n-1)\left[\frac{1}{R_1} - \frac{1}{R_2} + \frac{(n-1)CT}{nR_1R_2}\right]$$

where n is the refractive index of the lens material.

In the low power lenses of the present invention, the radius of the inner surface is less than the radius of the outer surface of the lens, and the lens is meniscus in shape. As $R_2$ decreases with $R_1$ constant, the lens has more minus power. When $R_2=R_1-CT$, the front and back surfaces of the lenses become concentric, at a power that is determined by the base curvature and center thickness of the lens. For example, in a 6 base or 9 base lens, the front and back surfaces of the lens become concentric at the following powers, for lenses of these center thicknesses:

TABLE 1

Power at Which Minus Power Lens Becomes Concentic For Given Base Curve and Center Thickness

| Base Curve | Center Thickness (mm) | Power (diopters) |
| --- | --- | --- |
| 9 Base | 1.5 | −0.16 |
|  | 2.0 | −0.22 |
|  | 2.5 | −0.28 |
| 6 Base | 1.5 | −0.07 |
|  | 2.0 | −0.10 |
|  | 2.5 | −0.13 |

As the inner radius ($R_2$) continues to decrease, the lens becomes progressively more minus, and the posterior surface becomes more concave. For the low minus power lenses of the present invention, CT is the thickest portion of the lens. For greater minus power lenses, CT will either be the same thickness as the rest of the lens ($R_2=R_1-CT$), or CT will be the thinnest portion of the lens ($R_2<R_1-CT$).

High base lenses used in contemporary eyewear produce their own undesired optical effects, because the curvature of the lens can induce prism, with yoked and vergence demands, as well as astigmatic blur. Such highly curved lenses are further optically distorted by the high wrap and pantoscopic tilt used in contemporary eyewear, which induces prism by tilt that varies across the lens. The present invention minimizes such distortion by introducing minus power into the lens, and rotating the optical axis, for example with respect to the center of curvature $C_1$ (of the anterior surface of the lens) to deviate the optical axis away from the line of sight. The optical axis is deviated in a direction generally opposite the incline of the lens toward the face.

The lens could also be rotated about the center of curvature $C_2$ (of the posterior surface of the lens), but this would shift the apex position for any lens other than a concentric lens, and is a less efficient method of achieving the stated goals. The lens is ideally rotated about $C_1$, but can rotate about a point along the optical axis, for example at $C_2$, or slightly away from the optical axis, such that the rotation angle is within 5 degrees of the optimal position for the given power and base curvature, preferably within 1 degree. However, the deviated optical axis passes through the centers $C_1$ and $C_2$ in spherical designs, but in aspheric and other designs may pass between $C_1$ and $C_2$, or near one of $C_1$ or $C_2$ (for example within a sufficient distance to reduce the optical inaccuracies in accordance with the present invention by using a deviated axis).

Figure 10:
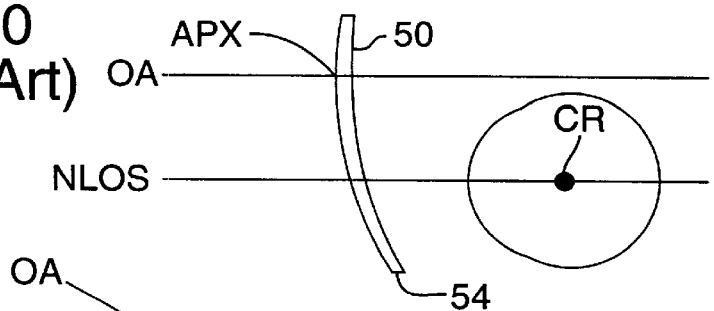
FIG. 10 is a vertical sectional view through a lens mounted with pantoscopic tilt, showing the problem of the prior art in which an optical centerline was oriented parallel to the normal line of sight.

The deviated line of sight of the present invention contrasts with inadequate prior art efforts to solve this problem, shown in FIG. 10, which is a vertical sectional view through a plano (zero power) lens 50 mounted with pantoscopic tilt in front of an eye having a center of rotation CR. The pantoscopic tilt moves the bottom edge 54 of the lens toward the face, which induces base down prism in the lens. The prior art attempted to address this problem by shifting the optical axis (OA) of the lens to a position spaced from and parallel to the LOS (FIG. 10). This did help minimize prismatic distortion along the LOS, but was inadequate to improve peripheral optical performance.

Figure 11:
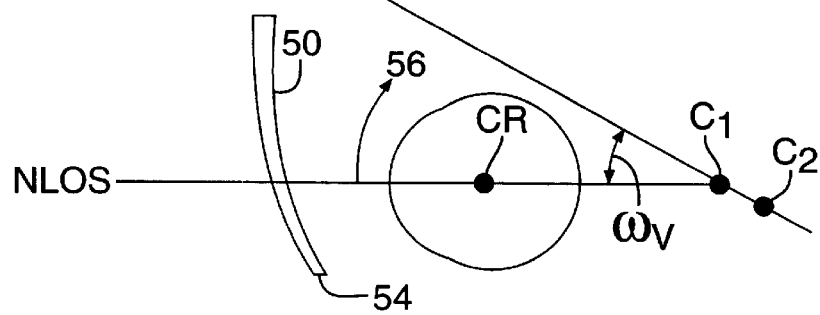
FIG. 11 is a view similar to FIG. 10, but showing the solution of the present invention in which the optical axis of a low power lens is deviated away from the line of sight.

The present invention solved this problem (as shown in FIG. 11) by abandoning the parallel relationship, and instead rotating the OA in a vertical direction around one of the centers of curvature (such as $C_1$) through an angle $\omega_v$ in a superior direction 56 away from the LOS (which for convenience in the drawing is shown as the NLOS, although it can be any FLOS). The direction 56 is selected to be away from the edge 54 that is inclined toward the face. The magnitude of angle $\omega_v$ at which minimum prism occurs can vary depending on the properties of the lens and its position relative to the LOS, but even minimal rotation of the OA in direction 56 will begin to neutralize the prism induced by the pantoscopic tilt. Equations for determining an optimum angle for absolute minimum distortion are provided later in this specification.

Figure 12:
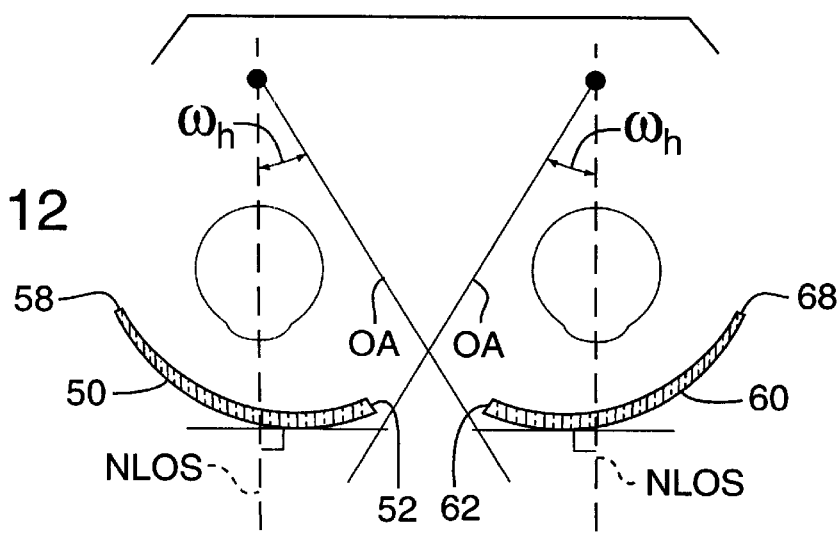
FIG. 12 is a horizontal sectional view through high wrap, low power lenses of the present invention, showing horizontal (nasal) deviation of the optical axis away from the line of sight to reduce optical distortion induced by the wrap.

The invention also includes eyewear and methods for reducing prism by tilt that is induced by lateral wrap of the lenses, as illustrated in FIG. 12, which is a horizontal section through a pair of lenses 50, 60. The lens 50 has a nasal edge 52 and a temporal edge 58, and the lens has lateral wrap at its temporal edge 58. The lens 60 has a nasal edge 62 and a temporal edge 68, and the lens has lateral wrap at its temporal edge 68. Instead of orienting the OA of each lens parallel to the LOS (which again for convenience is shown for the NLOS), the OA is rotated away from the LOS through an angle $\omega_h$ in a nasal direction generally opposite the direction of the lateral wrap. The specific optimal angle $\omega_h$ at which prismatic and other optical distortion is minimized depends on a number of factors, and will be illustrated in specific examples. However, deviation of the OA away from the LOS in the nasal direction progressively begins to minimize prism induced by the lateral wrap.

Figure 13:
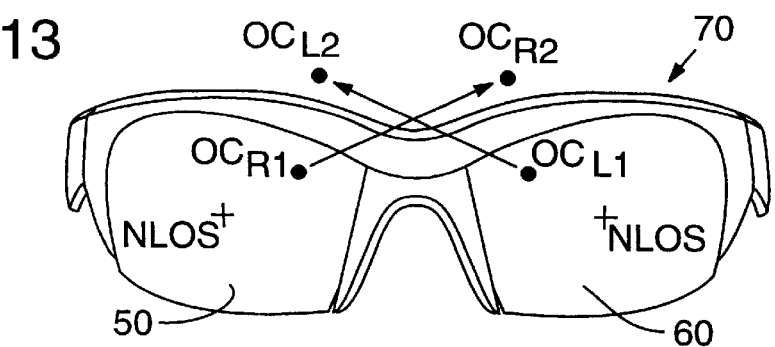
FIG. 13 is a front elevational view of the lenses of FIG. 12, mounted in dual lens eyewear, showing both nasal and superior deviation of the optical axis away from the line of sight.

FIG. 13 illustrates dual lens eyewear 70 in which the lenses are mounted with both lateral wrap and pantoscopic tilt. FIG. 13 also illustrates $OC_{R1}$ and $OC_{L1}$, which are the positions of the optical centers of the right and left lenses 50, 60 (respectively) of some prior art eyewear in which the OA is maintained parallel to the normal line of sight (NLOS). The optical centers $OC_{R2}$ and $OC_{L2}$ are the positions of the optical centers of the right and left lenses (respectively) after the wide angle rotation nasally and superiorly to minimize optical distortion induced by the lateral wrap and pantoscopic tilt.

Figure 14:
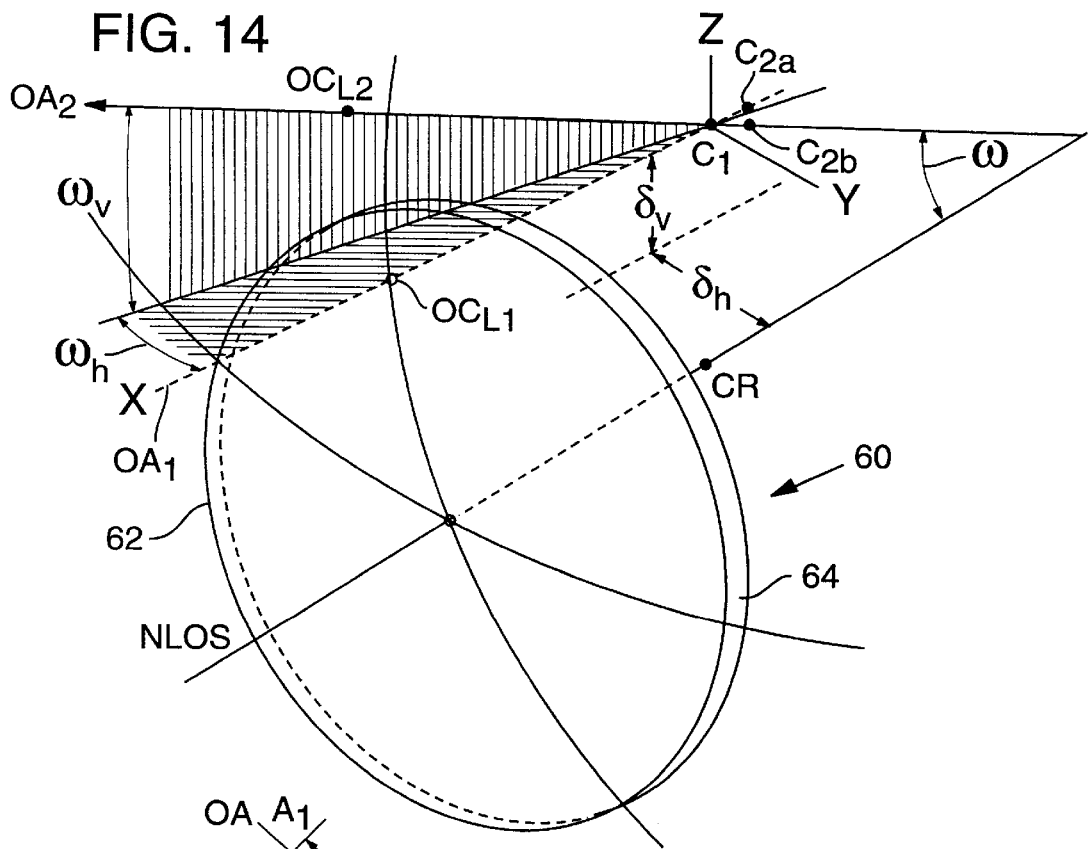
FIG. 14 is a perspective view of an isolated lens mounted with pantoscopic tilt and lateral wrap, showing superonasal deviation of the optical axis away from the line of sight with respect to the center of the sphere on which the front surface of the lens lies.

FIG. 14 further illustrates the superonasal deviation of the OA by depicting the left lens 60 of the eyewear 70 shown in FIG. 13, isolated from the frame, but maintaining the pantoscopic tilt and lateral wrap with which the lens was mounted in the frame. The lens 60 has front and back surfaces that substantially conform to the surfaces of a sphere (for example as measured by a lens clock to determine sphericity of a lens as understood in the art of ophthalmic lenses). The front surface of the lens substantially conforms to a first sphere having a center $C_1$, while the back surface of the lens substantially conforms to a second sphere having a center $C_2$. The theoretical NLOS is illustrated through the center of the lens, such that the NLOS further extends through the theoretical center of rotation CR of the eye.

The prior art location of the optical center $OC_{L1}$ of FIG. 13 is also illustrated in FIG. 14, in which the OC is spaced horizontally ($\delta_h$) and vertically ($\delta_v$) from the NLOS, so that the $OA_1$ extends through $C_1$ and $C_{2a}$ parallel to the NLOS. The present invention is a significant departure from that arrangement, in that the $OC_{L1}$ is moved through an angle $\omega_h$ in the X-Y plane (or has a component $\omega_h$) to compensate for the optical distortion induced by lateral wrap. The $OC_{L1}$ is also moved through an angle $\omega_v$ in the direction of the Z axis (or has a component $\omega_v$) so that the $OC_{L1}$ assumes the new position $OC_{L2}$ to compensate for the optical distortion induced by the pantoscopic tilt. In its new position, the $OC_{L2}$ is on an optical axis $OA_2$ that extends through the center $C_1$ of the first sphere and the new center $C_{2b}$ of the second sphere (where $C_{2b}$ has been rotated through opposite angles $\omega_h$ and $\omega_v$ from its original position $C_{2a}$ on the X axis). In this particular embodiment, the $OA_2$ intersects the NLOS at an angle $\omega$ (the resultant angle of components $\omega_h$ and $\omega_v$) that is described in greater detail in a later section of this specification. However, the ultimate effect is that the optical axis in this example is moved off of the lens, at an angle to the NLOS (or other FLOS) to offset the optical distortion induced by the wrap and tilt of the lens.

Some of the factors that enter into an optimal angle $\omega$ are illustrated in connection with FIG. 15, which may be viewed either as a horizontal cross-section of a left lens, or a vertical cross section of either a left or right lens. A horizontal cross sectional view of a right lens would be the mirror image of FIG. 15. The lens 100 has an anterior surface 102 that substantially conforms to a first sphere having a center $C_1$, and a posterior surface 104 that substantially conforms to a second sphere having a center $C_2$, wherein the surface 104 is displaced along the optical axis from the surface 102 by a distance that corresponds to the center thickness (CT) of the lens. The CT will be the thickest portion of the lens in a low minus power lens, and the thinnest portion of the lens at greater minus powers. The OA is arranged with respect to a wearer's LOS, for example a functional line of sight FLOS, so that the optical axis OA is tilted at an angle $\omega$ with respect to the FLOS. Angle $\omega$ is optimally chosen so as to minimize the total prismatic deviation of the lens when the wearer views along the FLOS. This optimal angle $\omega$ can be found, for example, by the relationship $$\omega = \sin^{-1}\left(\frac{\delta_2 - R_2 \sin\theta}{k}\right)$$

where $\delta_2$ is the distance between the FLOS and the apex line AL, $R_2$ is the radius of curvature of the posterior surface of the lens, $\theta$ is the angle between the FLOS and the radius of curvature of either the anterior ($\theta_1$) or posterior ($\theta_4$) surfaces of the lens, and k is the separation of the centers of curvature of the anterior and posterior surfaces of the lens.

Figure 15:
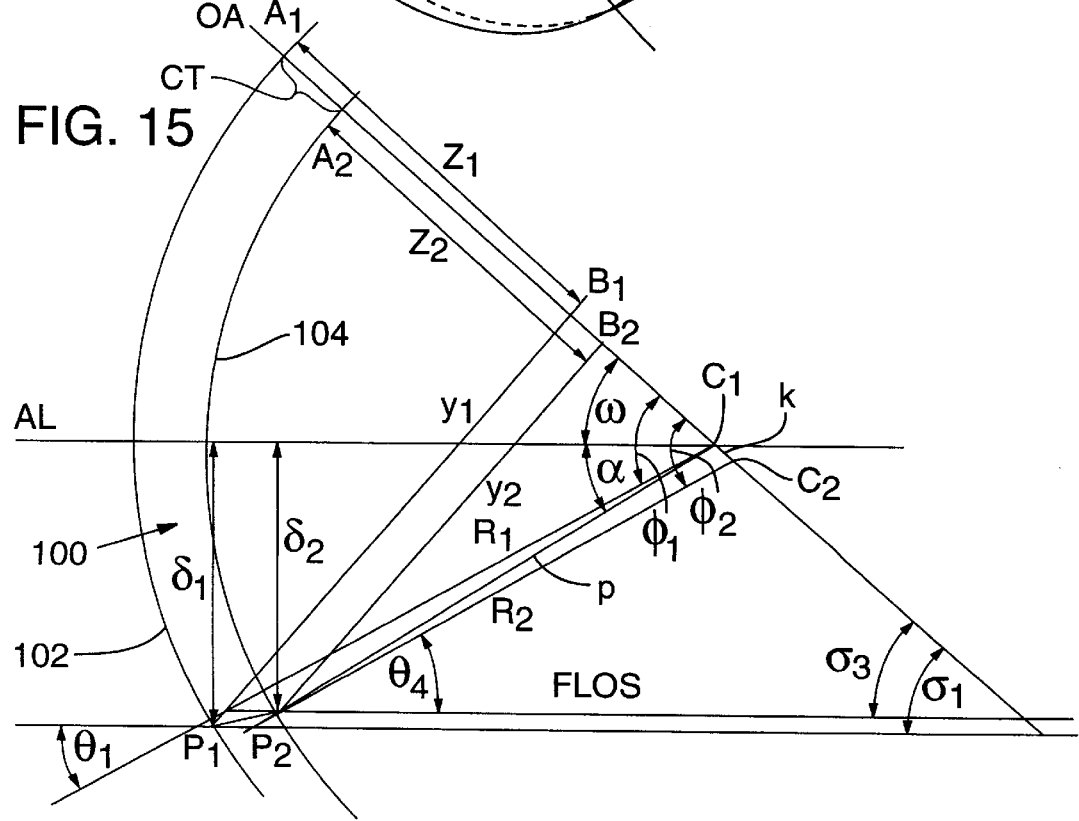
FIG. 15 is a schematic view illustrating either the horizontal or vertical geometric relationships of a lens having an optical axis deviated to optimally reduce optical distortion in the lens.

This equation can be better understood by an analysis of the following optical relationships in the ideal lens of the preferred embodiment shown in FIG. 15. The FLOS is displaced a distance $\delta_2$ from an apex line AL parallel to the FLOS, wherein AL extends through the center of curvature $C_1$ and the apex of the lens. The FLOS extends through the posterior surface 104 of the lens 100 at a point $P_2$, that is on a line p through the center of curvature $C_1$ and at an angle $\omega+\alpha$ from the optical axis OA, where $$\alpha = \sin^{-1}\left(\frac{\delta_2}{p}\right),$$

$$p = \overline{C_1 P_2} = (R_2^2 + k^2 - 2R_2 k \cos(\omega + \theta_4))^{1/2},$$

$$\theta_4 = \sin^{-1}\left(\frac{\delta_2 - k\ \sin\omega}{R_2}\right), \text{ and}$$

$$k = \overline{C_1 C_2} = R_2 + CT - R_1.$$

Pantoscopic tilt may be defined as the angle between the apex plane (previously shown in FIG. 5) and the tangent to the lens surface at the intersection of the lens surface and the FLOS. In FIG. 15, if FLOS coincides with NLOS, then the tangent planes at $P_1$ and $P_2$ are parallel, and the pantoscopic tilt angle is given by either $\tan^{-1}(\delta_{1v}/R_1)$ or $\tan^{-1}(\delta_{2v}/R_2)$ where $\delta_{1v}$ and $\delta_{2v}$ represent the vertical separation of the FLOS and the apex line (AL) with respect to the anterior and posterior surfaces respectively. If FIG. 15 represents a horizontal cross section of the lens, and FLOS is coincident with the NLOS, then the lateral wrap angle is similarly defined and given by $\tan^{-1}(\delta_{1h}/R_1)$ or $\tan^{-1}(\delta_{2h}/R_2)$ where $\delta_{1h}$ and $\delta_{2h}$ represent the horizontal separation of the FLOS and the apex line (AL) with respect to the anterior and posterior surfaces respectively.

By providing the lens 100 with a low power, and substantially tilting and decentering the lens with respect to the FLOS, superior optical performance can be obtained. The low power lens reduces the taper of the lens, as compared to a zero power lens, and this reduced taper in turn reduces optical distortion induced across the field of view by the changing relationship of the surfaces of a more tapered lens. Increased minus power can also be accompanied by an increase in the angle $\omega$, and an increase in the angle $\omega$ can be accompanied by a decrease in the base curve of the lens, to maintain optimum performance of the lens. The effect of some of these interrelated variables is illustrated in the following Examples.

EXAMPLE 1

A 6 base lens was made having the following optical characteristics, where the parameters are those shown in FIG. 15:

$R_1$=87.17 mm $R_2$=86.00 mm

CT=1.60 mm

P=−0.045 D

Panto about 12.5 degrees

Wrap about 15 degrees

|   | Horizontal | Vertical |
|---|---|---|
| $\delta$ | 23.35 mm | 19.05 mm |
| $\omega$ | 22.60 deg | 18.00 deg |

Both $\delta$ and $\omega$ are displaced in the nasal direction horizontally and in the superior direction vertically. The calculated prism and astigmatism for this lens along the NLOS and at 45 degrees temporal and nasal angles of gaze to the NLOS were compared to the predicted prism and astigmatism for a similar 6 base, −0.045 power lens that had the optical center at the apex of the lens (as in FIG. 10 where the OA extends through the APX), and a 6 base zero power (piano) lens with the OC at the apex. These prismatic deviations as described previously give the yoked and vergence demands.

TABLE 2

Prismatic Deviations for Base 6 Eyewear
Comparing Plano and Low Minus Power With and Without OA Rotated

| Lens Description | Viewing angle | Calculated Prism | Calc. Astigmatism |
|---|---|---|---|
| Zero Power | NLOS | 0.010 BI | 0.002 D |
| OC @ Apex | 45 ° nasal | 0.820 BO | 0.111 D |
| (OA Parellel to NLOS) | 45 ° temporal | 0.546 BI | 0.025 D |
| $\omega = 0$ ° | Vergence demand at 45 ° is 0.274 BO | | |
|  | Yoked demand at 45 ° is 0.546 pd | | |
| P = −0.045 D | NLOS | 0.113 BO | 0.006 D |
| OC @ Apex | 45 ° nasal | 0.771 BO | 0.136 D |
| (OA Parallel to NLOS) | 45 ° temporal | 0.339 BI | 0.019 D |
| $\omega = 0$ ° | Vergence demand at 45 ° is 0.432 BO | | |
|  | Yoked demand at 45 ° is 0.339 pd | | |
| P = −0.045 D | NLOS | 0.000 | 0.003 D |
| OC rotated away | 45 ° nasal | 0.576 BO | 0.099 D |
| from parallel to NLOS | 45 ° temporal | 0.400 BI | 0.024 D |
| $\omega = 22.6$ ° | Vergence demand at 45 ° is 0.176 BO | | |
|  | Yoked demand at 45 ° is 0.400 pd | | |

These results show that a low power lens with a rotated optical axis, in accordance with the present invention, is able to substantially eliminate prism along the NLOS (from 0.010 pd in the zero power non-rotated lens to 0.000 pd in the low power rotated lens), and substantially reduce vergence demand peripherally at 45° (from 0.274 to 0.176 pd BO), and also substantially reduce yoked demand peripherally at 45° (from 0.546 to 0.400 pd).

EXAMPLE 2

A 9 base lens was made having the following optical characteristics, where the parameters are those shown in FIG. 15:

$R_1$=58.9 mm $R_2$=57.9 mm

CT=1.5 mm

P=−0.075 D

Panto about 10 degrees

Wrap about 18 degrees

|  | Horizontal | Vertical |
| --- | --- | --- |
| δ | 18.5 mm | 10.0 mm |
| ω | 16 ° | 8.5 ° |

Optical performance parameters of eyewear incorporating a left and a right lens using this orientation of the lens are based on calculations and measurements that are collected in Table 3. Performance parameters are also set forth for comparison eyewear having both plano and low power lenses with optical axes through the apex and parallel to (and nasally spaced 18.5 mm from) the NLOS. Procedures for exact optical ray tracings to confirm these calculations are well known and are described in, for example, Warren Smith, *Modern Optical Engineering* (1966).

The vergence demand of the eyewear is calculated from the prismatic deviations at the nasal and temporal viewing angles. In eyewear as worn, if the right eye is viewing at an angle of 45° nasally with respect to the NLOS, then the left eye is viewing at about 45° temporally. These prismatic deviations as described previously give the yoked and vergence demands.

TABLE 3

Prismatic Deviations for Base 9 Eyewear
Comparing Plano and Low Minus Power With and Without OA Rotated

| Lens Description | Viewing Angle | Calculated Prism (pd) | Calculated Astigmatism |
| --- | --- | --- | --- |
| Zero Power | NLOS | 0.006 BI | 0.007 D |
| OC @ Apex | 45 ° Nasal | 1.370 BO | 0.234 D |
| δ = 18.5 mm | 45 ° Temporal | 0.953 BI | 0.046 D |
| ω = 0 ° | vergence demand at 45 ° is 0.417 BO | | |
|  | yoked demand at 45 ° is 0.953 pd | | |
| P = −0.075 D | NLOS | 0.152 BO | 0.014 D |
| OC @ apex | 45 ° Nasal | 0.887 BO | 0.174 D |
| δ = 18.5 mm | 45 ° Temporal | 0.420 BI | 0.019 D |
| ω = 0 ° | vergence demand at 45 ° is 0.467 BO | | |
|  | yoked demand at 45 ° is 0.420 pd | | |
| P = −0.075 D | NLOS | 0.000 | 0.005 D |
| OC rotated | 45 ° Nasal | 0.685 BO | 0.129 D |
| δ = 18.5 mm | 45 ° Temporal | 0.502 BI | 0.026 D |
| ω$_h$ = 16 ° | vergence demand at 45 ° is 0.184 BO | | |
|  | yoked demand at 45 ° is 0.502 pd | | |

Table 3 shows that conventional (decentered plano, P=0, ω=0) eyewear exhibit small amounts of prismatic deviation along the NLOS; for the base 9 eyewear of Table 3, the prismatic deviation along the NLOS is about 0.006 BI. However, it has been previously unappreciated that these plano lenses produce large prismatic deviations in peripheral portions of the lenses. When viewing through these lenses at 45° nasally and 45° temporally from the NLOS, the prismatic deviations in the individual lenses are large (about 1.37 pd BO and 0.95 pd BI, respectively) and produce a large vergence demand of 0.417 BO.

Decentered minus eyewear produce prismatic deviations even when the NLOS is parallel to the optical centerline. The decentered minus eyewear (P=−0.075 D, δ=18.5 mm, ω=0°) exhibit a prismatic deviation of about 0.15 BO along the NLOS. When viewing at angles of 45° nasally and 45° temporally with respect to the NLOS, the prismatic deviations are about 0.89 BO and 0.42 BI, respectively. The magnitudes of the prismatic deviations at the extreme nasal and temporal angles are smaller than those of the plano eyewear and the vergence demand is larger, but not significantly so. The decentered minus eyewear is particularly well-suited for applications requiring monocular vision with low levels of prismatic deviation with respect to angles of gaze away from the NLOS.

By combining a nasal rotation of the OA (ω=16°) with a nasal decentration of δ=18.5 mm of the optical axis OA, the rotated, decentered minus eyewear exhibits no prismatic deviation along the NLOS. When viewing at angles of 45° temporally and nasally from the NLOS, the prismatic deviations are about 0.69 BO and 0.50 BI. These prismatic deviations are smaller than those of the other eyewear and produce a significantly smaller vergence demand of 0.18 BO, and yoked demand of 0.50 pd.

Table 3 also contains calculated values of astigmatism. Values of astigmatism of less than 0.12 D are generally considered acceptable. For example, the ANSI sunglasses standard (ANSI Z80.3) permits 0.12 D of astigmatism in nonprescription eyewear along the NLOS. Table 3 illustrates that the low minus, rotated OA eyewear of the present invention also has less astigmatic blur than tilted decentered plano eyewear or tilted, decentered minus eyewear.

For purposes of comparison, the rotated, decentered, low minus eyewear is compared to a lens in which P=0, but for which base curvature and δ vary as shown. For an equal amount and direction of rotation, for a given base curvature and decentration, wherein the rotated, decentered, minus eyewear exhibits zero prism along the LOS, the zero power rotated decentered eyewear would have the following prism values along the LOS:

6 Base: 0.28 Base In; $δ_h$=23.35 mm
7 Base: 0.285 Base In; $δ_h$=23.35 mm
8 Base: 0.252 Base In; $δ_h$=18.5 mm
9 Base: 0.291 Base In; $δ_h$=18.5 mm When situated in eyewear, these lenses would require between 0.5 and 0.58 pd of divergence when the wearer views a distant object along the NLOS. This amount and direction of prismatic distortion is potentially very disturbing to most wearers. The plano decentered, non-rotated lenses produce very low prism along the NLOS, while low minus power decentered, non-rotated lenses produce Base Out prism along the NLOS. The decentered, OA rotated lenses of the present invention, are capable of reducing prism along the FLOS (including the NLOS) to substantially zero (for example less than 0.1 pd or 0.05 pd), and even eliminating prism along the FLOS to zero.

EXAMPLE 3

General Approach to Designing Rotated OA Lens

This general scheme for designing a lens with a rotated (angularly deviated) OA is set forth in this Example, with particular reference to FIGS. 14 and 15, where the AL is the apex line that extends from $C_1$ through the apex of the lens. The lens 100 may first be arranged so that the LOS (such as a FLOS, or particularly a NLOS) is parallel to the optical axis OA, and offset horizontally by $δ_H$ and vertically $δ_V$. The OA is then rotated generally horizontally by the angle $ω_H$ in a substantially nasal direction, and generally vertically by the angle $ω_V$ in a substantially superior direction (for lenses with lateral wrap and pantoscopic tilt) so that the optical axis OA is tilted away from the LOS. Such rotations of the OA may be accomplished by moving the outline of a lens (or a lens blank) on a sphere as described in FIG. 16A. Although the angles of rotation of the OA are given in horizontal and vertical components for convenience, the deviation can also occur in a single superonasal direction without tracing out the horizontal and vertical components of the displacement.

FIG. 15 depicts a representative lens with an optical axis OA intersecting the anterior and posterior surfaces 102, 104 of a lens. However, in lenses for eyewear according to the invention, the OA of the lens does not necessarily pass through either the lens blank from which the lens is cut, or the lens as cut for insertion into a frame. The decentrations and substantial tilts of the lens from the NLOS are still measured from the optical axis. Although the optical center is not on the cut lens or the lens blank, the optical center is readily located by extending the curvature of the anterior surface of the lens until it intersects the optical axis.

Representative embodiments of the invention described above pertain to base 6 and base 9 eyewear, but the invention is not limited to these base curvatures. Generally, a lens is selected for eyewear based upon an apex location and a base curvature of the lens. The apex location and the base curvature are usually determined by the frame and may be selected for appearance or eye protection. The radius of curvature of the posterior surface $R_2$ and the center thickness CT of the lens are then varied to produce a small amount of power, for example, minus power. For lens materials such as polycarbonate, the center thickness CT generally is greater than 1 mm so that the lens is strong and durable, but other or future materials and methods of manufacture may allow for a thinner lens.

The lens may then be decentered so that the optical axis of the lens is parallel to the FLOS and passes through the functional apex. Next the lens may be rotated through an angle ω about the center of curvature of the anterior surface ($C_1$). The prismatic deviation along the FLOS is then calculated, and may be confirmed by measurement. Angle ω may be adjusted until the total deviation along the LOS approaches a minimum, preferably less than 0.12 prism diopters along the LOS and less than 0.9 prism diopters at 45 degrees nasally and temporally, more specifically less than 0.1 prism diopters along the line of sight, most suitably about 0 prism diopters along the line of sight. The vergence demand of the lens is suitably less than 0.4 prism diopters, and ideally less than 0.3 or 0.2 prism diopters.

While several mathematical methods may be employed to calculate the total deviation, the most efficient requires solving the problem in reverse by starting with a known eye position and determining the precise position of the object that the eye views, as outlined below. Referring to FIG. 15, the visual angle is identified as the direction of gaze with respect to the FLOS, which in FIG. 15 is zero degrees. This direction of gaze intersects the posterior surface 104 of the lens 100 at $P_2$. The distance from $B_2$ to P2 along a line perpendicular to the optical axis OA is designated $y_2$; the distance from $A_2$ to $B_2$ along the optical axis OA is designated $z_2$, which is the sagittal depth with respect to the posterior surface; $\phi_2$ is the angle between the normal to the posterior surface and the optical axis OA; and $\sigma_3$ is the angle between the direction of gaze and the optical axis OA (which is the same as ω when FLOS=NLOS). The direction of gaze with respect to the normal to the posterior surface is given by angle $\theta_4$, where $$\theta_4 = \Phi_2 - \sigma_3.$$

The direction of gaze prior to refraction at the posterior surface with respect to the normal at the posterior surface is given by angle $\theta_3$ (not shown in FIG. 15) using Snell's law, where n is the index of refraction of the lens material and $$\theta_3 = \sin^{-1}\left(\frac{\sin\theta_4}{n}\right).$$

The direction of gaze prior to refraction at the posterior surface with respect to the optical axis is given by angle $\sigma_2$ (not shown in FIG. 15), where $$\sigma_2 = \Phi_2 - \theta_3.$$

Then calculate the point of intersection $P_1$ of this refracted ray and the anterior surface 102 of the lens 100, where $y_1$ is the distance between $P_1$ and the optical axis OA at $B_1$ along a line perpendicular to the optical axis OA, and $z_1$ is the sagittal depth of $P_1$ with respect to the anterior surface:

$$y_1 = (2R_1 z_1 - z_1^2)^{1/2} \text{ and}$$

$$z_1 = b - \left(b^2 - \left[\frac{\sigma_1 \tan^2 \sigma_2}{\tan^2 \sigma_2 + 1}\right]\right)^{1/2}, \text{ where}$$

$$b = (s_1 \tan^2 \sigma_2 + R_1)/(\tan^2 \sigma_2 + 1)$$

$$s_1 = (y_2/\tan\sigma_2) + z_2$$

Then calculate $\phi_1$ as the angle between the normal to the anterior surface and the optical axis OA using $$\phi_1 = \tan^{-1}\left(\frac{y_1}{R_1 - z_1}\right).$$

The direction of gaze with respect to the normal to the anterior surface is given by angle $\theta_2$ (not shown in FIG. 15), where $$\theta_2 = \Phi_1 - \sigma_2.$$

The direction of gaze prior to refraction at the anterior surface with respect to the normal to the anterior surface is given by angle $\theta_1$ once more using Snell's law and the index n defined previously:

$$\theta_1 = \sin^{-1}(n \sin \theta_2)$$

The direction of gaze prior to refraction at the anterior surface with respect to the optical axis OA is given by angle $\sigma_1$, where $$\sigma_1 = \Phi_1 - \theta_1$$

Finally, the total deviation ε is given by the difference between angles $\sigma_1$ and $\sigma_3$. If these angles are given in degrees, the following equation gives ε in prism diopters:

$$\varepsilon = \frac{(\sigma_3 - \sigma_1)}{100} \times \frac{\pi}{180}$$

If the prismatic deviation along the NLOS is not sufficiently small, then the rotation angle ω or the lens power is changed. If the prismatic deviation is base-out, the angle of rotation ω is increased or the magnitude of the minus power is reduced. If the prismatic deviation is base-in, the angle of rotation ω is decreased or the magnitude of the minus power increased. The lens power and the angle of rotation can be selected to reduce the prismatic deviation along the NLOS. For example, the angle of rotation can be selected to be greater than 30°, greater than 20°, greater than 15°, between 20° and 40°, or between 15° and 30°.

EXAMPLE 4

This Example shows some optimal relationships between the base curvature, center thickness of the lens, and the low minus power of the lens that optimally minimizes prismatic distortion along the LOS. The following Table illustrates the nasalward rotation of the optical axis that produces zero prism along the LOS with changes in decentration for the following lenses:

6 Base: center thickness 1.6 mm, power −0.045 D
7 Base: center thickness 1.5 mm, power −0.051 D
8 Base: center thickness 1.5 mm, power −0.063 D
9 Base: center thickness 1.5 mm, power −0.075 D

TABLE 4

Rotation of OA for Varying Decentrations and Base Curvature

| Decentration | 6 Base | 7 Base | 8 Base | 9 Base |
|---|---|---|---|---|
| 0 mm | 0 deg | 0 deg | 0 deg | 0 deg |
| 5 mm | 4.5 deg | 4.2 deg | 4.2 deg | 4.2 deg |
| 10 mm | 9.0 deg | 8.5 deg | 8.5 deg | 8.5 deg |
| 15 mm | 13.8 deg | 13.0 deg | 13.0 deg | 13.0 deg |
| 20 mm | 18.9 deg | 17.8 deg | 17.8 deg | 17.7 deg |
| 25 mm | 24.6 deg | 23.0 deg | 22.9 deg | 22.8 deg |

This table generally illustrates that the rotation of the OA away from the LOS, which is required to neutralize the prism along the LOS, increases as the decentration increases, and that generally the angle of rotation decreases as the base curvature of the lens increases.

EXAMPLE 5

This example illustrates the nasalward rotation of the optical axis that maintains zero prism along the line of sight with changes in center thickness for the following lenses:

6 Base: nasal decentration 23.35 mm, power −0.045 D
7 Base: nasal decentration 23.35 mm, power −0.051 D
8 Base: nasal decentration 18.5 mm, power −0.063 D
9 Base: nasal decentration 18.5 mm, power −0.075 D The nasal decentration is a function of lateral wrap. Generally, the radius of curvature of the posterior surface of the lens decreases as CT increases for each base curve to maintain constant power and zero prism along the line of sight.

TABLE 5

Rotation of OA for Varying Center Thickness and Base Curvatures

| Center Thickness | 6 Base | 7 Base | 8 Base | 9 Base |
|---|---|---|---|---|
| 1.2 mm | — | — | 31.6 deg | 29.3 deg |
| 1.4 mm | 36.0 deg | 25.2 deg | 19.5 deg | 19.0 deg |
| 1.6 mm | 22.8 deg | 17.7 deg | 14.5 deg | 14.5 deg |
| 1.8 mm | 16.6 deg | 14.2 deg | 11.6 deg | 11.5 deg |
| 2.0 mm | 13.6 deg | 11.6 deg | 9.6 deg | 9.7 deg |
| 2.2 mm | 11.3 deg | 9.8 deg | 8.2 deg | 8.4 deg |
| 2.4 mm | 9.6 deg | 8.7 deg | 7.2 deg | 7.3 deg |
| 2.6 mm | 8.6 deg | 7.6 deg | 6.3 deg | 6.5 deg |
| 2.8 mm | 7.55 deg | 6.75 deg | 5.7 deg | 5.9 deg |
| 3.0 mm | 6.75 deg | 6.25 deg | 5.2 deg | 5.3 deg |

Generally, as the center thickness of the lens increases, the angle ω decreases for a lens of a given base curvature, power and decentration.

EXAMPLE 6

This example illustrates how the angle ω can change to maintain calculated zero prism for a lens having a CT=1.5 mm, decentration=18.5 mm, for lenses of varying base curvatures and powers.

TABLE 6

Rotation of OA for Varying Base Curvatures and Powers

| Base Curve | Power (D) | | | | |
| | −0.02 | −0.04 | −0.06 | −0.08 | −0.10 |
|---|---|---|---|---|---|
| 6 | 4.5 deg | 15.2 deg | — | — | — |
| 7 | 3.6 deg | 9.9 deg | 24.6 deg | — | — |
| 8 | 2.8 deg | 7.35 deg | 15.0 deg | 32.5 deg | — |
| 9 | 2.3 deg | 5.9 deg | 10.7 deg | 18.7 deg | 44.0 deg |

These examples illustrate that as base curve increases for a given CT and δ, the angle ω decreases for a given low power lens. For a given base curve, the angle also increases as greater minus power is provided by the lens.

EXAMPLE 7

Cutting Lenses from Lens Blanks

Figure 16A:
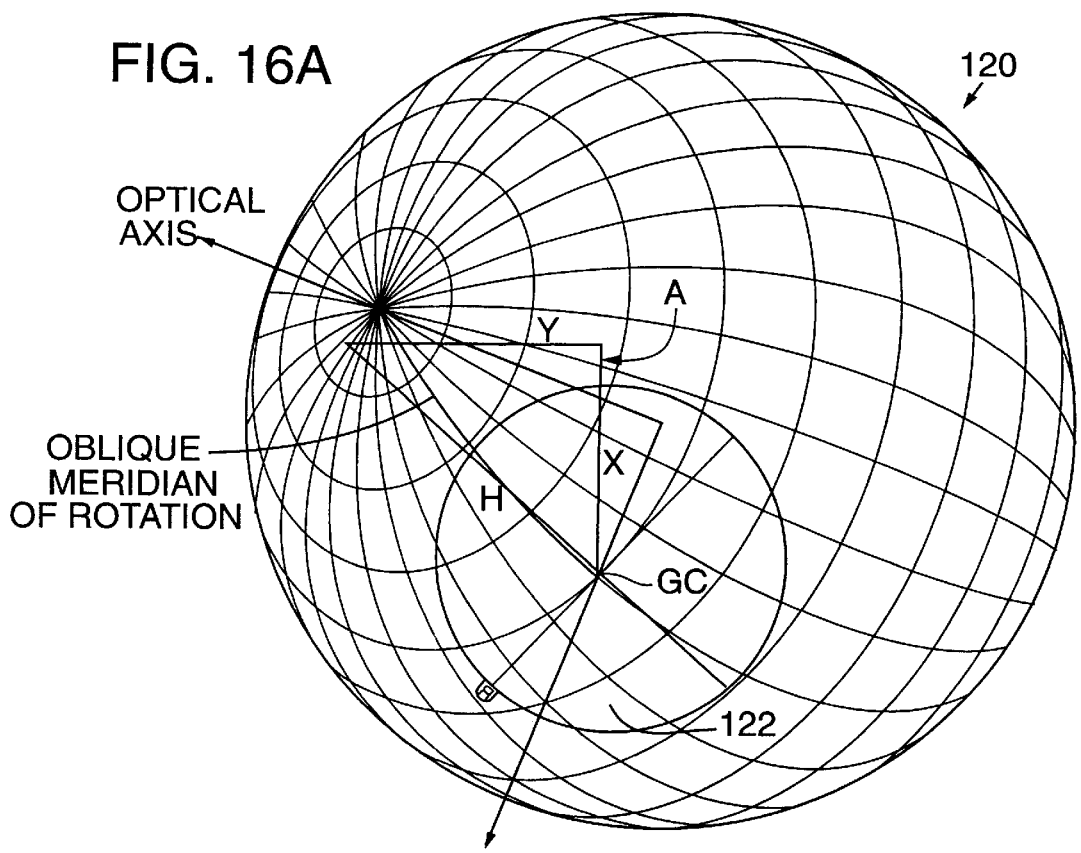
FIG. 16A is a schematic view of a lens blank positioned on a sphere, illustrating the position from which the lens blank would be cut in accordance with the present invention, and showing displacements of the lens blank projected on to a frontal plane.
Figure 16B:
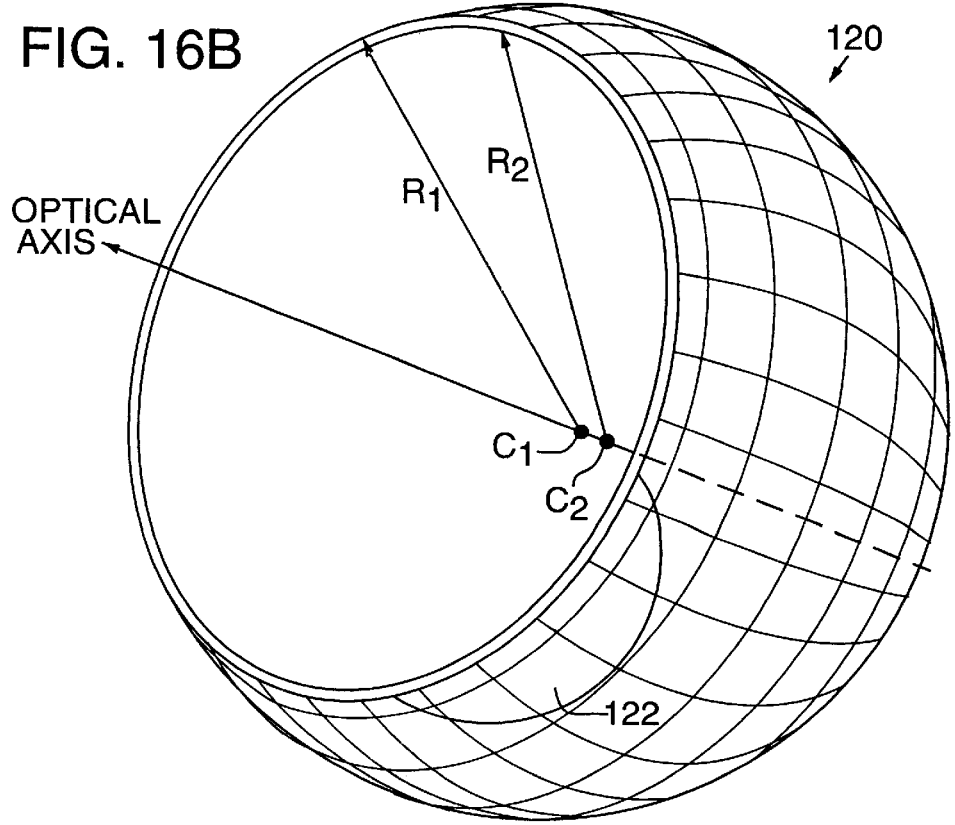
FIG. 16B is a view similar to FIG. 16A, but showing the top portion of the sphere broken away.

Although the lenses of the present invention may be injection molded to an exact shape or ground and then cut, the lenses are preferably cut from an injection molded lens blank. For spherical lenses, the lens blank can be conceptualized as being cut from the shell of a sphere 120, as shown in FIG. 16A. The positions of the centers of curvature $C_1$ and $C_2$ and radii of curvature $R_1$ and $R_2$ (FIG. 16B), of the outer and inner surfaces of the sphere 120 respectively determine the power of the lens to be cut from the lens blank. The radius of curvature $R_1$ (of the outer surface of the shell) determines the base curvature of the lens. The optical axis OA extends through $C_1$ and $C_2$, and is shown projecting through a pole of the sphere. Once the desired amounts of lateral wrap and pantoscopic tilt of a lens are determined, a position can be located on the sphere that will provide a lens having those characteristics. The lens blank can then be formed that has the shape of that portion of the shell of the sphere.

In the embodiment illustrated in FIG. 16A, the lens blank 122 is formed with a shape corresponding to the shell of the sphere at the depicted location, in which the optical axis does not extend through the lens blank itself. Hence, the optical center of the lens blank is not on the blank itself, but is instead on an imaginary extension of the blank at the pole of the sphere. The blank 122 is positioned so that a lens to be cut from the lens blank will have a selected LOS (such as a FLOS, e.g. the NLOS) that is at the desired angle ω to the optical axis OA, for a lens of a given low minus power and base curvature. In FIG. 16A, the blank is shown displaced from the pole by distances X, Y and H that are projected on to a frontal plane A. In this particularly disclosed embodiment of a base 6 lens, the geometric center GC of the blank 122 is displaced a distance of 54.5 mm in a direction Y along a vertical meridian of the sphere, and a distance of 42.0 mm in a direction X along a latitudinal line (parallel to the equator). The net displacement of the GC from the OC of the sphere is therefore a distance H of 68.8 mm.

Figure 17:
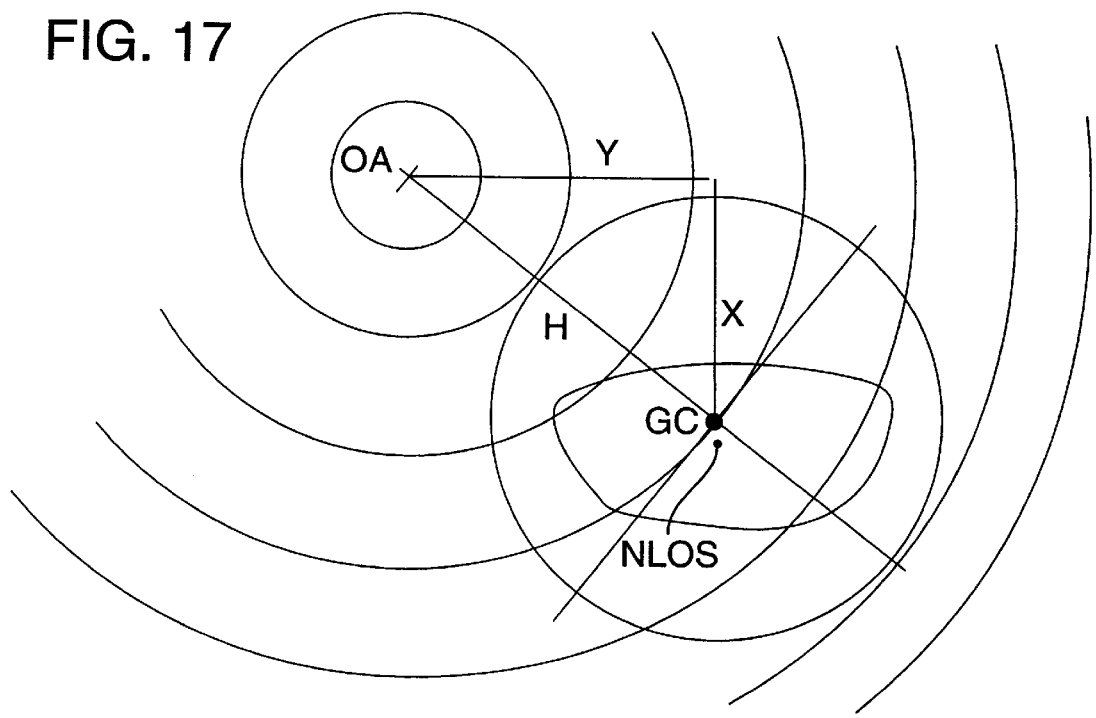
FIG. 17 is a two-dimensional view of the sphere of FIG. 16A.

FIG. 17 is a two dimensional view of FIG. 16A, which further shows the position of a lens that is to be cut from the lens blank, illustrating the position of the NLOS and the geometric center GC of the lens blank with respect to the OA. This view shows the wide angle of deviation between the optical axis OA of the sphere and the GC of the lens blank, which are separated by an angle ω at $C_1$ (not shown in FIG. 17) that subtends an angle at the surface of the sphere demarcated by the distance H on the sphere surface.

EXAMPLE 8

Efficient Use of Lens Blanks

Figure 18:
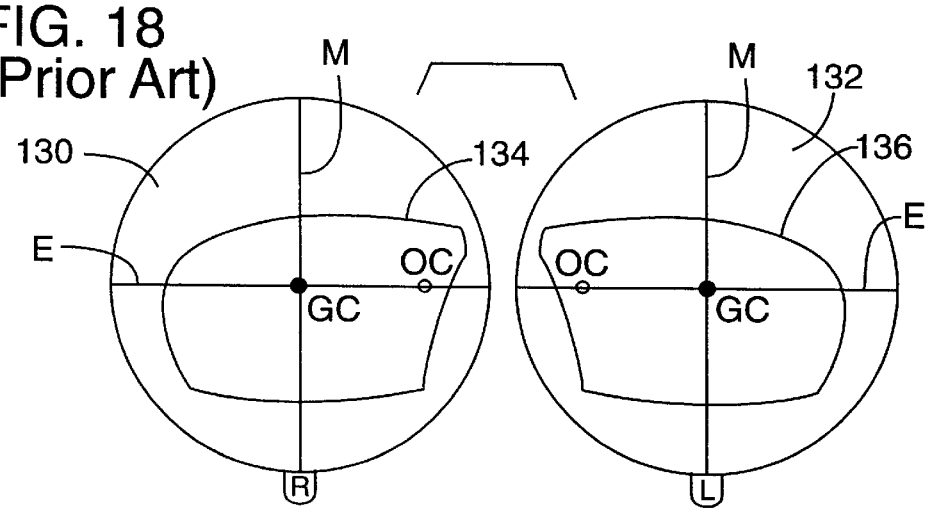
FIG. 18 is a front elevational view of a lens outline projected on to a lens blank, illustrating the position from which the lens is cut from the lens blank to horizontally decenter the lens in the prior art.

The present invention also includes a method of more efficiently using lens blanks than in the prior art, while maintaining superior optical performance of the lens cut from the blank. The problem of the prior art is illustrated in FIG. 18, which shows a right lens blank 130 and a left lens blank 132 which are injection molded. Each of the lens blanks has a geometric center GC, and an optical center OC displaced along an equator E of the lens blank toward a medial edge of the blank. The lens blank therefore tapers vertically symmetrically (in a superoinferior direction along meridian M) from the equator E.

One of the problems with an injection molded blank is that there are often injection molding artifacts peripherally in the lens, and particularly at the injection "gate" where plastic is injected into the mold prior to hardening. The optical irregularities introduced by these artifacts can often be avoided by cutting a lens 134 or 136 from the lens blank 130, 132 at a central position on the lens blank, away from the peripheral irregularities. Lenses 134, 136 are shown in FIG. 18 to be cut from the center of the lens blank to avoid these optical irregularities.

Figure 19:
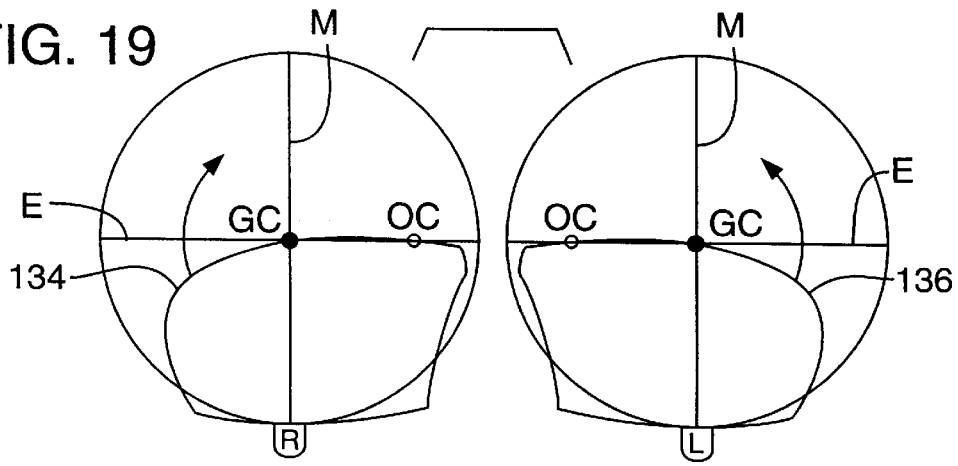
FIG. 19 is a view similar to FIG. 18, but showing the lens outline displaced into the lower half of a lens blank to vertically decenter the lens from the position shown in FIG. 18.

FIG. 19 shows a problem that is encountered if the lenses 134, 136 are to be vertically optically decentered by shifting the lens vertically downward on the lens blank. If the amount of vertical decentration approaches the B dimension of the lens, then peripheral portions of the lens will not fit on the lens blank. This will necessitate the expensive step of using a larger lens blank. Even if the lens is small enough to fit on the lens blank (which it is not in FIG. 19), the lens must be cut from optically irregular, peripheral portions of the blank.

Figure 20:
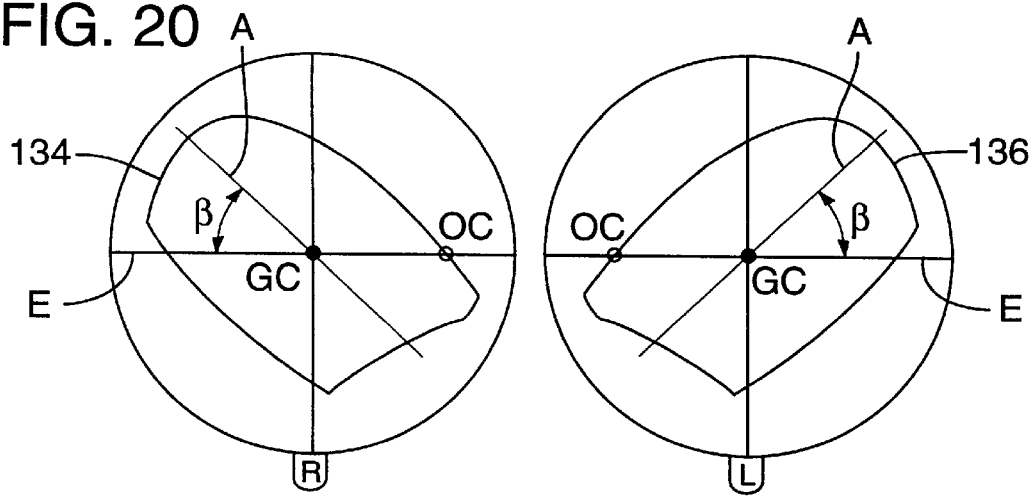
FIGS. 20–22 are front elevational views of one aspect of the present invention, in which the lens has been rotated from the position shown in FIG. 19, so that the optical center of the lens can be adjusted both horizontally and vertically, while more efficiently using the lens blank material.

FIG. 20 shows the solution of the present invention, which permits a horizontal and vertical decentration of the same extent as in FIG. 19, but without the problems encountered in that example. FIG. 20 shows that the lens outlines in FIG. 19 can be rotated in the direction of the arrows in FIG. 19, around the optical centers OC, so that the A line of the lens outline is at a non-zero acute angle $\beta$ to the A line. The OC is still located at the upper edge of the lens, however the body of the lens outline has now been rotated into a central area of the blank that is freer of optical irregularities. This rotation also permits the extremely vertically decentered lens and/or horizontally decentered lens to be cut from a lens blank without having to increase the diameter of the blank to accommodate the decentered lens.

Hence the lens can be rotated without changing the optical characteristics of the lens (such as power and center thickness) when the lens is rotated on the surface of the blank around an axis defined by the optical axis. The magnitude of the angle $\beta$ through which the lens is rotated can vary widely, depending on the size of the lens and the desired degree of vertical decentration. In the illustrated embodiment of FIG. 20, the angle $\beta$ is approximately 30–40°, although the angle could, for example, be 5–90°, more particularly 10–80°, or greater than 10 or 20 degrees, and less than 90°.

Figure 21:
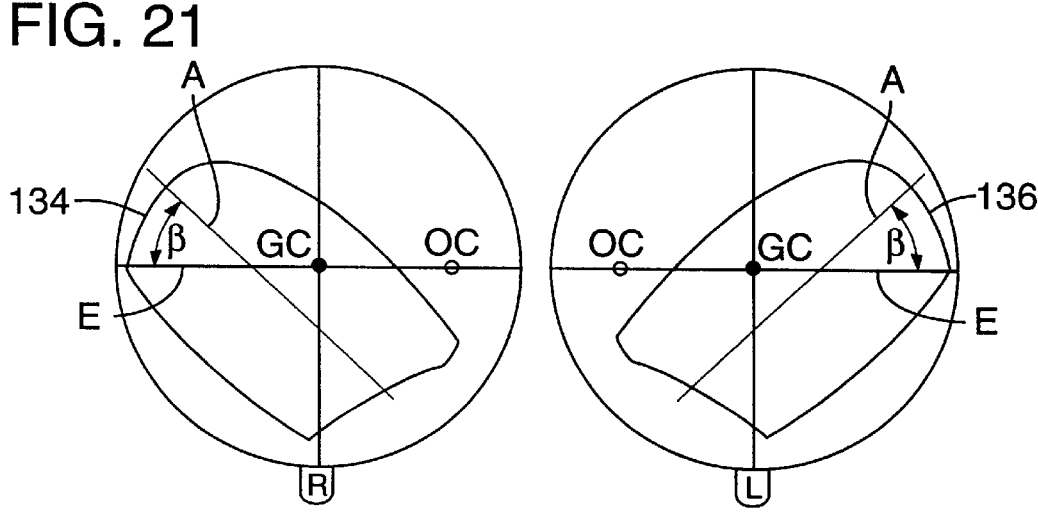

FIG. 21 further illustrates the versatility of the method by showing that an extreme vertical decentration, in which the OC is not even on the lens, can be achieved by rotating the lens outline from the position shown in FIG. 19 to the position shown in FIG. 20, and then further displacing the lens outline in a direction perpendicular to the A line. As can be appreciated by comparing FIG. 19 with FIG. 21, the extent of vertical decentration achieved in FIG. 21 could not be obtained by the non-rotated method of FIG. 19. If the simple displacement of the lens along the vertical meridian M (as in FIG. 19) were not accompanied by the rotary maneuver of the present invention, the lens would project partially off of the lens blank. Hence it would not be possible to cut the lens from the lens blank, without increasing the diameter or other dimensions of the lens blank.

Figure 22:
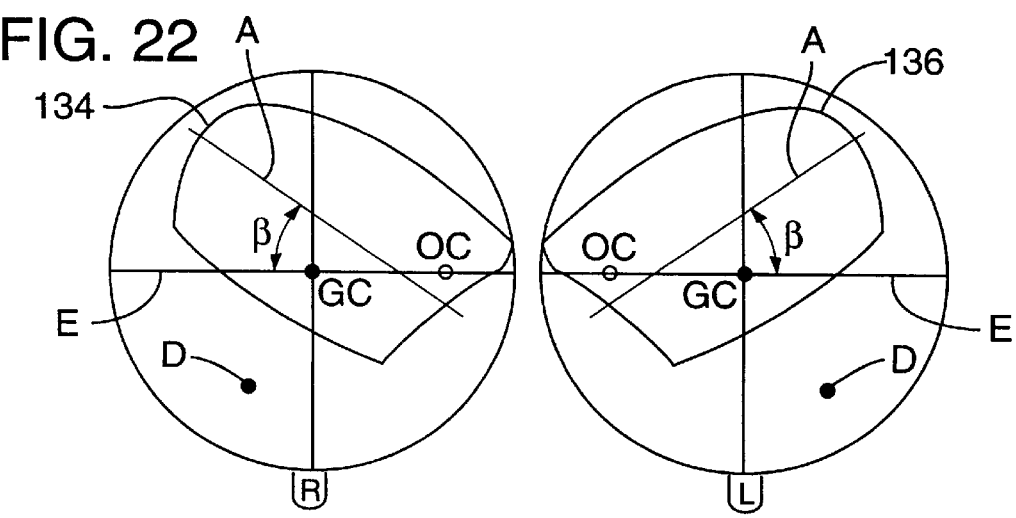

FIG. 22 further illustrates the versatility of the rotational method, showing that even a lens that does not have vertical decentration can be rotated around the OC to cut it from a more convenient portion of the blank, for example to avoid a defect D in the blank that would otherwise interfere with the optical quality of the lens cut from the blank.

Figure 23:
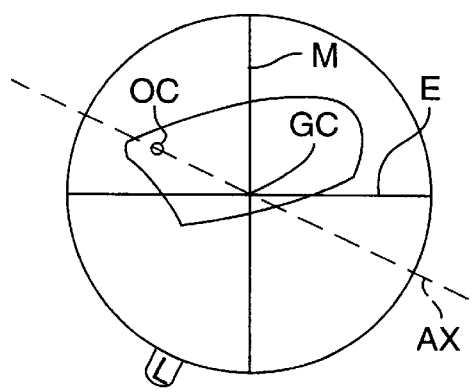
FIG. 23 is a view similar to FIGS. 20–22, but showing the optical center of the lens blank above its equator.

FIG. 23 demonstrates that the optical center OC need not be on the equator E of the lens blank (where the equator is a horizontal bisector of the blank that does not define a line of symmetry about which the blank vertically tapers). Instead the axis of symmetry from which the blank symmetrically tapers superiorly and inferiorly is the axis AX in FIG. 23, which extends through the GC of the blank, at a non-zero acute angle to the equator E.

Figure 24:
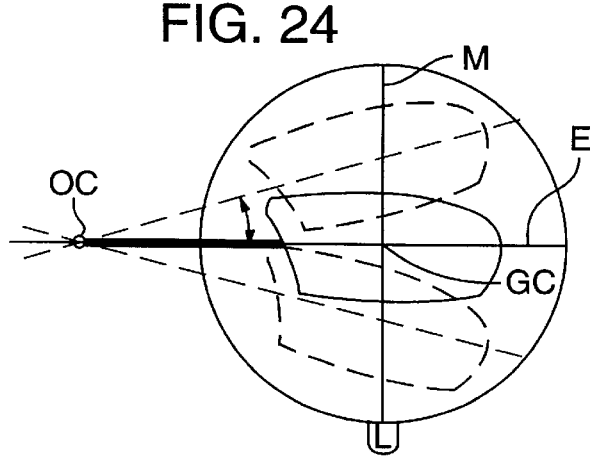
FIGS. 24 and 25 are views similar to FIGS. 20–22, but showing a lens blank in which the optical center is not located on the lens blank.

FIG. 24 demonstrates a lens blank in which the OC is not on the blank, which is a common situation in the manufacture of lenses described in this specification that have large angles of deviation between the optical axis and line of sight. The lens outline does not have to be centered over the GC of the lens blank, but can be en bloc rotated with respect to the OC. Such en bloc rotation can be visualized, for example, by imagining a fixed arm extending from the OC to the nasal edge of the lens in FIG. 24. The lens outline can then be moved by rotating the rigid arm around the OC, but without changing the position of the lens outline relative to the rigid arm. Two possible positions to which the lens outline can be rotated are shown in phantom in FIG. 24, which provide a lens of the same shape and with the same location of the OC in the lens.

Figure 25:
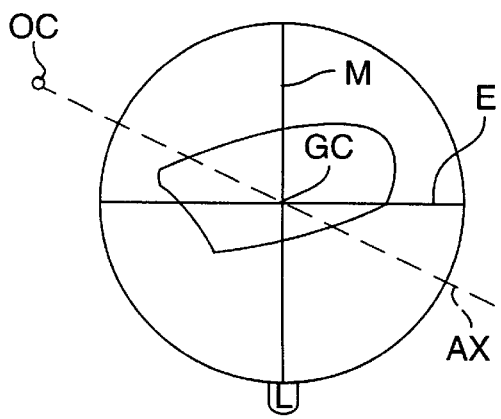

FIG. 25 shows another lens blank with the OC off the blank, but in which the OC is both vertically displaced from the equator E and horizontally displaced from the vertical meridian M.

Wrap and Pantoscopic Tilt

Figure 26:
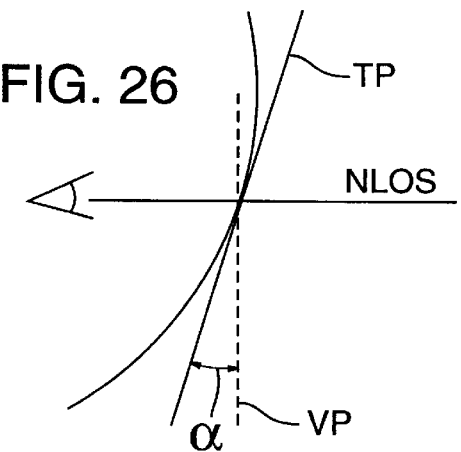
FIG. 26 is a schematic side view illustrating how pantoscopic tilt is measured in a lens.

FIG. 26 is a schematic vertical sectional view which illustrates that pantoscopic tilt is determined by measuring the angle $\alpha$ between a frontal vertical plane VP that is perpendicular to the FLOS (such as the NLOS) and extends through the point at which the FLOS/NLOS intersects the lens, and a tangent plane TP that is tangent to the point at which the FLOS/NLOS intersects the anterior surface of the lens. For a lens having a base curvature of 9, the pantoscopic tilt $\alpha$ of the lens may, for example, be in the range of 1–30°, for example 3–20° or 8–14°, and more particularly 8–12°. The degree of tilt may also vary depending on the head and facial morphology of the person wearing the eyewear. Europeans and European-Americans, for example, have less prominent cheeks, more prominent brows, and higher nasions than Asians and Asian-Americans, and can tolerate more pantoscopic tilt. Exemplary pantoscopic tilt angles are shown in Table 7.

Figure 27:
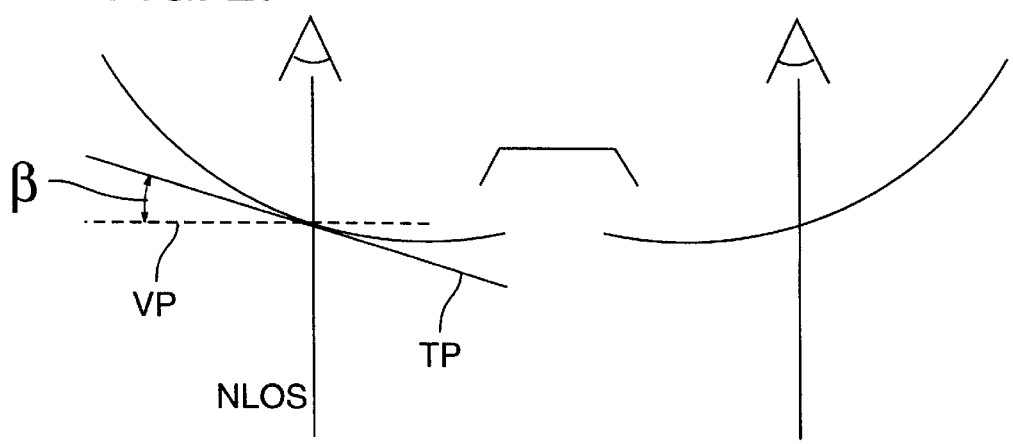
FIG. 27 is a schematic top view illustrating how lateral wrap is measured in a lens.

FIG. 27 is a schematic horizontal view which illustrates that lateral wrap is determined by measuring the angle $\beta$ between the frontal vertical plane VP and the tangent plane TP. As with pantoscopic tilt, examples of the degree of wrap are shown in Table 7.

TABLE 7

Wrap and Panto Angles in Non-Asians and Asians

|  | Non-Asian | Asian |
|---|---|---|
| Lateral Wrap | 5–30 ° | 5–20 ° |
| Panto | 5–20 ° | 3–15 ° |

Lenses may have wrap and panto angles outside of these ranges. The angles given in Table 7 are merely exemplary, and smaller and larger angles of tilt can be compensated for by the present invention.

The lenses are preferably made of polycarbonate, but may also be made from other impact resistant material such as CR-39.

When a lens is deviated "away" from a direction the lens is tilted, the direction of deviation need not be exactly opposite the direction of tilt, but can be a direction that generally reduces the undesired optical distortions discussed herein.

Abbreviations

APX: apex
AL: apex line
CR: center or rotation
CT: center thickness
DBC: distance between centers
FAPX: functional apex
FA: functional apex plane
FLOS: functional line of sight
FP: frontal plane
GC: geometric center
LOS: line of sight
LP: Listing's plane
MP: median plane
NLOS: normal line of sight
OA: optical axis
OC: optical center
TP: Tangent plane
VP: vertical frontal plane Having illustrated and demonstrated the principles of the invention in several embodiments, it should be apparent to those skilled in the art that these embodiments can be modified in arrangement and detail without departing from such principles. We claim as the invention all that comes within the scope of these claims.

We claim:

1. A low minus power noncorrective lens to be mounted in a frame to support the lens in front of an eye in an as worn orientation, the lens having at least two opposing edges with at least one of the opposing edges closer to the face than the other opposing edge, wherein the lens has an optical axis that is angled, with respect to a normal line of sight, away from the edge that is closer to the face and away from parallel with the normal line of sight to reduce prismatic distortion.

2. The lens of claim 1, wherein the optical axis is angled away from parallel with the normal line of sight at an angle that reduces prismatic distortion along the line of sight and peripherally in the lens.

3. The lens of claim 1, wherein the optical axis is angled away from parallel with the normal line of sight at an angle that reduces astigmatic blur along the line of sight and peripherally in the lens.

4. The lens of claim 1, wherein the optical axis is angled away from parallel with the normal line of sight at an angle that reduces yoked prismatic effect and vergence demand of lateral peripheral gaze, as compared to a lens in which the optical axis and normal line of sight are spaced and parallel to one another.

5. The lens of claim 4, wherein the lens in the as worn position has pantoscopic tilt with an inferior edge of the lens closer to the face than a superior edge of the lens, and the optical axis is deviated generally superiorly.

6. The lens of claim 4, wherein the lens in the as worn position has lateral wrap, and the optical axis is deviated generally nasally.

7. The lens of claim 4, wherein the lens in the as worn position has pantoscopic tilt and lateral wrap, and the optical axis extends generally superiorly and nasally from the normal line of sight.

8. The lens of claim 1, wherein the low minus power lens is more than −0.005 D minus.

9. The lens of claim 8, wherein the low minus power lens is more than −0.01 D minus.

10. The lens of claim 1, wherein the optical axis extends horizontally and vertically away from the normal line of sight, the lens is low minus power and is to be mounted with lateral wrap and pantoscopic tilt, and the optical axis extends at an angle with respect to a center of curvature of an anterior surface of the lens, generally superiorly and nasally to reduce prismatic distortion along the normal line of sight.

11. The lens of claim 10, wherein the lens is a spherical lens in which an anterior surface of the lens substantially conforms to a first sphere having a first center of curvature, and a posterior surface of the lens substantially conforms to a second sphere having a second center of curvature, and the optical axis extends through the first and second centers of curvature and through an optical center of the lens, wherein the optical center of the lens is displaced from the normal line of sight to minimize prismatic distortion along the normal line of sight of the lens.

12. The lens of claim 10, wherein the lens has a minus power of −0.01 to −0.12.

13. The lens of claim 10, wherein the lens has a minus power of −0.04 to −0.09.

14. The lens of claim 10, wherein an anterior surface of the lens conforms substantially to the surface of a first sphere having a first center of curvature, and a posterior surface of the lens conforms substantially to the surface of a second sphere having a second surface of curvature, and a radius of the first sphere is greater than a radius of the second sphere.

15. The lens of claim 14, wherein the lens is a high base lens.

16. The lens of claim 15, wherein the lens is at least a base 6 lens.

17. The lens of claim 16, wherein the lens is at least a base 8 lens.

18. The lens of claim 17, wherein the lens is at least a base 9 lens.

19. The lens of claim 1, wherein the lens is for dual lens eyewear.

20. The lens of claim 1, wherein the lens is cut from a lens blank in which the optical center of the lens blank is not on the lens blank.

21. The lens of claim 1, wherein the lens is cut from a lens blank in which an optical center of the lens blank is on the lens blank, but not the lens that is cut from the lens blank.

22. The lens of claim 1, wherein the lens is cut from a lens blank in which an optical center of the lens blank is on the lens that is cut from the lens blank.

23. A high base lens to be mounted in dual lens, protective, noncorrective eyewear, with the lens mounted in a frame for holding the lens in an as worn orientation in which a tangent plane at a reference line of sight is angled to a vertical plane the lens comprising:

a substantially spherical anterior surface that substantially conforms to a first sphere having a first center, and a substantially spherical posterior surface that substantially conforms to a second sphere having a second center, wherein a radius of the first sphere is greater than a radius of the second sphere, so that a lens thickness tapers away from an optical center of the lens, and an optical axis extends through the first and second centers of the spheres and the optical center of the lens, wherein the lens has a low minus power, and the optical axis is angled to the reference line of sight, in a direction that reduces prismatic distortion.

24. The lens of claim 23, wherein the as worn orientation of the lens includes lateral wrap, and the optical axis is angled away from parallel with the reference line of sight in a nasal direction.

25. The lens of claim 24, wherein the lens is mounted with lateral wrap in the as worn orientation with an angle of 5–30° between the tangent plane at the reference line of sight and the vertical plane, and the optical axis of the lens is at an angled away from parallel at an angle of 10–25° to the line of sight.

26. The lens of claim 23, wherein the tangent plane in the as worn orientation of the lens angles away from the vertical plane in a superior direction from the reference line of sight to provide the lens with pantoscopic tilt, and the optical axis is angled away from parallel with the line of sight in a superior direction as the optical axis extends from the first and second centers of the spheres toward the lens.

27. The lens of claim 26, wherein the lens is mounted with pantoscopic tilt in the as worn orientation with an angle of 3–20° between the tangent plane and the vertical plane, and the optical axis of the lens is angled away from parallel at an angle of 5–20° to the reference line of sight.

28. The lens of claim 23, wherein the tangent plane in the as worn orientation of the lens angles away from the vertical plane in a lateral direction from the reference line of sight to provide the lens with lateral wrap, and the tangent plane further angles away from the vertical plane in a superior direction from the reference line of sight to provide the lens with pantoscopic tilt, and the optical axis is angled away from parallel with the line of sight in both a nasal and superior direction between the first and second centers of the spheres and the lens.

29. The lens of claim 23, wherein the lens is a 6 base lens with a center thickness of about 1.6 mm, and a power of about −0.045 diopters, and the as worn orientation of the lens includes lateral wrap of about 15°, a pantoscopic tilt of about 12°, and the optical axis of the lens is angled away from parallel to the reference line of sight at about 22–23 degrees nasally and 18–19 degrees superiorly.

30. The lens of claim 23, wherein the optical axis extends at an angle $\omega$ from the parallel with the reference line of sight, wherein $$\omega = \sin^{-1}\left(\frac{\delta - R_2 \sin\theta}{k}\right)$$

where $\delta$ is the distance between the line of sight and an apex line, $R_2$ is a radius of curvature of the rear surface of the lens, $\theta$ is an angle between the reference line of sight and a radius of curvature of either the anterior or posterior surface of the lens when the reference line of sight coincides with the normal line of sight, and k is a separation of the centers of curvature of the first and second spheres.

31. A noncorrective, protective, lens mounted in dual lens eyewear with pantoscopic tilt, such that a tangent plane at a normal line of sight extends at an angle $\alpha$ with respect to a vertical plane, and with lateral wrap such that the tangent plane at the normal line of sight extends at an angle $\beta$ with respect to the vertical plane, wherein:

the lens is a low power minus lens having −0.02 to −0.12 diopters power, a center thickness of 1.0–3.0 mm, a base curvature of 6–9, lateral wrap with an angle $\beta$ of 5–30°, and pantoscopic tilt with an angle $\alpha$ of 3–20°, and a substantially spherical anterior surface that substantially conforms to a surface of a first sphere having a first center, and a substantially spherical posterior surface that substantially conforms to a surface of a second sphere having a second center, wherein a radius of the first sphere is greater than a radius of the second sphere, so that a lens thickness tapers away from an optical center of the lens, and an optical axis of the lens extends through the first and second centers of the spheres and the optical center of the lens, and the optical axis is angled to extend nasally and superiorly away from the normal line of sight, to substantially offset prismatic distortion induced by the lateral wrap and pantoscopic tilt of the lens, as compared to a lens having an identical power center thickness, base curvature, lateral wrap and pantoscopic tilt in which the optical axis is spaced from and parallel to the normal line of sight.

32. The lens of claim 31, wherein the lens is a base 6 lens, has a center thickness of about 1.6 mm, a power of −0.045, pantoscopic tilt with an angle $\alpha$ of about 12° and lateral wrap with an angle $\beta$ of about 15°, and the optical axis extends nasally about 22–23 degrees and superiorly about 18–19 degrees with respect to the line of sight.

33. A method of manufacturing a non-corrective lens that is to be mounted in a tilted as worn orientation in a frame, the method comprising:

providing a low power lens of a selected center thickness and base curvature; and cutting the lens from a lens blank at a position such that an optical axis of the lens is to be horizontally and vertically displaced from a reference line of sight, and angularly deviated to the reference line of sight at an angle that offsets at least some of the prismatic distortion introduced into the lens by the tilted as worn orientation.

34. A method of cutting a lens from a lens blank, wherein the lens blank has an equatorial line that extends through a geometric center and an optical center of the lens blank, and the optical center of the lens blank is offset from the geometric center of the lens blank, the method comprising cutting the lens with an A line that extends through the geometric center of the lens and horizontally bisects the lens, wherein the A line is angled with respect to the equatorial line of the lens blank.

35. The method of claim 34, wherein the lens is to be mounted in an as worn orientation with the optical center of the lens horizontally and vertically displaced from a reference line of sight, and the lens is cut from the lens blank with a lens outline shifted downward on the lens blank to raise the optical center to a superior portion of the lens outline, and the lens outline is rotated around the optical center of the lens blank so that the A line of the lens outline is at a nonzero angle to the equatorial line of the lens blank, without substantially changing a shape of the lens.

36. A method of manufacturing a right lens for dual lens optically corrected eyewear mounted in an as worn orientation with wrap and pantoscopic tilt, the method comprising:

providing a lens blank, the lens blank having a thickness which is vertically tapered symmetrically on either side of an equatorial line that extends through a geometric center of the lens blank, the lens blank further being horizontally tapered from a relatively greater thickness at an optical center located between the geometric center of the lens blank at a medial edge of the blank to a relatively lesser thickness at a lateral edge of the lens blank, the equatorial line dividing the lens blank into an upper half and a lower half, and cutting the lens from the lens blank such that the lens is rotated with respect to the optical center, without substantially changing geometric and optical characteristics of the lens.

37. A method of cutting a lens from a lens blank, comprising:

providing a lens blank having spherical front and back surfaces, each of which tapers symmetrically from an optical center of the lens blank, and an equator of the lens blank that extends through the optical center of the lens blank and a geometric center of the lens blank;

determining a lens outline on the lens blank such that a lens cut from that lens outline would provide the optical center of the lens blank at a desired position of the optical center on the lens to be cut from the lens blank, with the optical center of the lens horizontally and/or vertically offset from a geometric center of the lens;

rotating the lens outline around the optical center of the lens blank, to select one or more of a plurality of potential lens outlines in which the lens shape is equivalent;

wherein the lens outline has an A line that extends through the geometric center of the lens, and the lens is cut from the lens blank with the A line angled to the equator of the lens blank.

38. A lens cut from a lens blank by the method of claim 37.

39. A method of manufacturing noncorrective, dual lens eyewear exhibiting wrap and pantoscopic tilt, the method comprising:

obtaining a lens blank comprising an inner surface conforming to a first sphere having a first center, and an outer surface conforming to a second sphere having a second center offset from the first center, a vertically and horizontally tapered lens thickness defined between the inner and outer surfaces, and an optical axis passing through the first and second centers and an optical center of the lens blank;

selecting a desired lens shape and a position of an optical center of the lens; and while maintaining the optical center of the lens superimposed on the optical center of the lens blank, rotating the lens shape around the optical center of the lens blank to determine a plurality of potential positions of cutting the lens from the lens blank wherein the shape of the lens will be equivalent.

40. The method of claim 39, further comprising cutting the lens from one of the plurality of potential positions, wherein an A line through a geometric center of the lens is angled to an equator of the lens blank that extends through the geometric center and optical center of the lens blank.

41. The method of claim 40, wherein the lens is a low minus power lens, and the method further comprises mounting the lens to a frame such that the optical axis intersects a wearer's normal straight ahead line of sight at an angle that reduces prismatic distortion.

42. The method of claim 41, wherein mounting the lens to the frame comprises mounting two lenses to the frame.

43. A method of minimizing prismatic distortion in non-corrective eyewear, comprising:

providing a low minus power noncorrective lens mounted to a frame, wherein the lens has an inner surface conforming to a first sphere having a first center, and an outer surface conforming to a second sphere having a second center, and an optical axis that extends through the first and second centers and an optical center of the lens;

supporting the lens in front of an eye in a predetermined relationship with respect to a wearer's reference line of sight, wherein the lens is supported with wrap and pantoscopic tilt, and the optical axis extends at an angle to the line of sight that reduces prismatic distortion in the lens.

44. The method of claim 43, wherein the optical axis extends at an angle nasally and superior from one of the first and second centers to the lens.

45. The method of claim 44, wherein the optical axis extends at an angle at least 15° to the optical axis nasally and/or superiorly.

46. The method of claim 45, wherein the optical axis extends at an angle of at least 15° to the optical axis nasally and superiorly.

47. The method of claim 43, wherein the lens has a minus power of at −0.01 to −0.12.

48. Right and left low minus power noncorrective lenses mounted to a frame for holding the lens in front of the right and left eyes of a wearer with an optical axis of the lens in a fixed relationship to a normal line of sight of the wearer, wherein each lens has an inner surface having a first center of curvature, an outer surface having a second center of curvature, and an optical axis that extends through the first and second centers and through a corresponding optical center of each lens, wherein the lens is mounted to the frame with lateral wrap and pantoscopic tilt, and the optical center of each lens is displaced nasally and superiorly from the normal line of sight so that the optical axis of each lens is non-parallel to the normal line of sight, and extends at an angle to the normal line of site that diminishes prismatic distortion in the lens.

* * * * *